(12) United States Patent
Mylari

(10) Patent No.: US 6,894,047 B2
(45) Date of Patent: May 17, 2005

(54) TRIAZINE COMPOUNDS USEFUL AS SORBITOL DEHYDROGENASE INHIBITORS

(75) Inventor: Banavara L. Mylari, Waterfrod, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/107,763

(22) Filed: Mar. 26, 2002

(65) Prior Publication Data

US 2003/0004166 A1 Jan. 2, 2003

Related U.S. Application Data

(60) Provisional application No. 60/280,050, filed on Mar. 30, 2001.

(51) Int. Cl.⁷ .................... C07D 251/42; A61K 31/53; A61P 9/10
(52) U.S. Cl. .................... 514/245; 544/194; 544/212
(58) Field of Search ................... 544/194, 212; 514/245, 241

(56) References Cited

U.S. PATENT DOCUMENTS

| | | | |
|---|---|---|---|
| 3,583,986 A | 6/1971 | Heimberger et al. | 260/249.9 |
| 3,703,514 A | 11/1972 | Aron-Samuel et al. | 260/249.9 |
| 5,138,058 A | 8/1992 | Geisen et al. | 544/295 |
| 5,215,990 A | 6/1993 | Geisen et al. | 514/255 |
| 5,728,704 A | 3/1998 | Mylari et al. | 514/256 |
| 5,866,578 A | 2/1999 | Mylari et al. | 514/256 |
| 6,414,149 B1 * | 7/2002 | Chu-Moyer et al. | 514/241 |

FOREIGN PATENT DOCUMENTS

| | | |
|---|---|---|
| EP | 1041068 | 10/2000 |
| WO | WO0059510 | 10/2000 |

OTHER PUBLICATIONS

Obrosova et al., Diabetologia, 42(10): 1187–1194.*
U.S. Non–provisional Appl. No. 09/997,039, filed Nov. 29, 2001.
U.S. Non–provisional Appl. No. 09/974,414, filed Oct. 9, 2001.

Roger L. N. Harris, *The Synthesis of Triazines from N-Cyanoamidines*, Synthesis, Communications, Oct. 1980, p. 841–842.

* cited by examiner

*Primary Examiner*—Venkataraman Balasubramanian
(74) *Attorney, Agent, or Firm*—Gregg C. Benson; Peter C. Richardson; Martha A. Gammill

(57) ABSTRACT

This invention is directed to sorbitol dehydrogenase inhibitory compounds of formula I

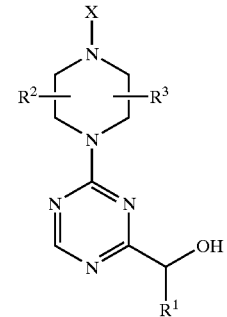

wherein $R^1$, $R^2$ and $R^3$ are as defined in the specification. This invention is also directed to pharmaceutical compositions containing these compounds and to methods of treating or preventing diabetic complications, particularly diabetic neuropathy, diabetic nephropathy, diabetic microangiopathy, diabetic macroangiopathy, diabetic cardiomyopathy and foot ulcers. This invention is also directed to pharmaceutical compositions comprising a combination of a compound of formula I of the present invention with a second pharmaceutical agent, including an aldose reductase inhibitor, a sodium hydrogen ion exchange inhibitor, a glycogen phosphorylase inhibitor, a selective serotonin reuptake inhibitor, a 3-hydroxy-3-methylglutaryl coenzyme A reductase inhibitor, an angiotensin converting enzyme inhibitor, a thiazolidinedione antidiabetic agent, an angiotensin II receptor antagonist, a γ-aminobutyric acid agonist, a phosphodiesterase type 5 inhibitor, an adenosine agonist, and a CETP inhibitor and to methods of using these compositions.

20 Claims, No Drawings

TRIAZINE COMPOUNDS USEFUL AS SORBITOL DEHYDROGENASE INHIBITORS

This application claims the benefit of U.S. Provisional Application No. 60/280,050, filed Mar. 30, 2001.

FIELD OF THE INVENTION

The present invention relates to novel triazine compounds of formula I, isomers thereof, prodrugs of said compounds or isomers, or pharmaceutically acceptable salts of said compounds, isomers or prodrugs, and to methods of using such compounds to inhibit sorbitol dehydrogenase (SDH), lower fructose levels or treat diabetic complications, such as diabetic neuropathy, diabetic retinopathy, diabetic nephropathy, diabetic cardiomyopathy, diabetic microangiopathy and diabetic macroangiopathy, in mammals. The present invention also relates to pharmaceutical compositions containing such triazine compounds. The present invention also relates to pharmaceutical compositions and kits comprising a combination of a sorbitol dehydrogenase inhibitor of formula I, an isomer thereof, a prodrug of said compound or isomer, or a pharmaceutically acceptable salt of said compound, isomer or prodrug, and a second pharmaceutical agent and to methods of using these combination compositions and kits.

BACKGROUND OF THE INVENTION

Triazine compounds of formula I, as defined below, and their pharmaceutically acceptable salts, lower fructose levels in the tissues of mammals affected by diabetes (e.g., nerve, kidney and retina tissue) and are useful in the treatment and prevention of the diabetic complications referred to above. These compounds, and/or their metabolites in vivo, are inhibitors of the enzyme sorbitol dehydrogenase, which catalyzes the oxidation of sorbitol to fructose.

Commonly assigned U.S. Pat. Nos. 5,728,704 and 5,866,578 disclose compounds of formula A

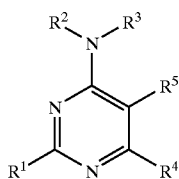

A wherein $R^1$ through $R^5$ are defined as disclosed therein, which are useful as sorbitol dehydrogenase inhibitors, having utility in the treatment of diabetic complications. Commonly assigned International Publication No. WO 00/59510 discloses aminopyrimidines as sorbitol dehydrogenase inhibitors. Commonly assigned published European Patent Application EP 1 041 068 discloses pyrimidine derivatives as sorbitol dehydrogenase inhibitors, useful for treating or preventing diabetic complications.

Commonly assigned U.S. non-provisional Ser. No. 09/974,414, filed Oct. 9, 2001, discloses pharmaceutical combinations of statins and sorbitol dehydrogenase inhibitors. Commonly assigned U.S. non-provisional Ser. No. 09/997,039, filed, Nov. 29, 2001, discloses the combination of a γ-aminobutyric acid (GABA) agonists and sorbitol dehydrogenase inhibitors.

U.S. Pat. Nos. 5,138,058 and 5,215,990 disclose piperazine substituted pyrimidine compounds, having utility as tools in screening for aldose reductase inhibitors due to the sorbitol accumulating activity of said compounds.

SUMMARY OF THE INVENTION

The present invention is directed to compounds of formula I

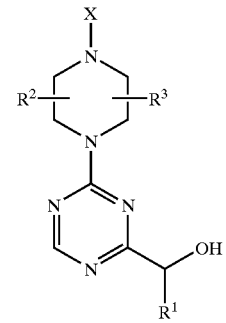

I an isomer thereof, a prodrug of said compound or isomer, or a pharmaceutically acceptable salt of said compound, isomer or prodrug;

wherein $R^1$ is a) hydrogen or b) —($C_1$–$C_4$)alkyl;

$R^2$ and $R^3$ are each independently a) hydrogen, b) —($C_1$–$C_4$)alkyl, c) —($C_3$–$C_6$)cycloalkyl or d) phenyl which for each occurrence is optionally substituted with one or two substituents, each substituent is independently selected from Group Q;

X is a) —C(O)—$R^4$-Z, b) —$SO_2$—$R^4$-Z, c) —C(O)—$NR^5R^6$, d) —$SO_2$—$NR^5R^6$ or e) 1,3,5-triazin-2-yl having $R^{z1}$ and $R^{z2}$ substituents;

$R^4$ is a) a covalent bond or b) —($C_1$–$C_4$)alkyl-;

Z is a) phenyl or benzyl wherein the phenyl ring in each of these groups is optionally substituted with one or two substitutents, each substituent is independently selected from Group Q, or b) Het;

$R^5$ and $R^6$ are each independently a) hydrogen, b) —($C_1$–$C_4$)alkyl or c) ($C_3$–$C_6$)cycloalkyl; or $R^5$ and $R^6$ are taken together along with the nitrogen atom to which they are attached to form pyrrolidinyl or piperidinyl;

Het is a) pyridyl, b) thiazolyl, c) oxazolyl, d) quinolyl, e) isoquinolyl, f) phthalizinyl, g) quinoxalyl, h) benzthiazolyl, i) benzoxazolyl, j) benzofuranyl, k) benzothienyl, l) furanopyridyl or m) thienopyridyl; wherein each of these groups is optionally substituted with one or two substituents, each substituent is independently selected from Group Q;

Group Q is a) fluoro, b) chloro, c) bromo, d) —($C_1$–$C_4$) alkyl, e) —($C_3$–$C_6$)cycloalkyl, f) —O—($C_1$–$C_4$)alkyl, g) —S—($C_1$–$C_4$)alkyl, h) —$SO_2$—($C_1$–$C_4$)alkyl, i) hydroxy or j) —($C_1$–$C_4$)alkyl-hydroxy;

$R^{z1}$ and $R^{z2}$ are each independently selected from a) hydrogen, b) hydroxy, c) chloro, d) —($C_1$–$C_4$)alkyl, e) —($C_3$–$C_6$)cycloalkyl, f) —O—($C_1$–$C_4$)alkyl, g) —($C_1$–$C_4$) alkyl-O—($C_1$–$C_4$)alkyl, h) —CHO, i) —C(O)—($C_1$–$C_4$) alkyl, j) —($C_1$–$C_4$)alkyl-hydroxy, k) phenyl which for each occurrence is optionally substituted with one or two substitutents, each substituent is independently selected from Group Q, l) pyrroyl, m) imidazolyl or n) triazolyl.

More particularly, the present invention provides such compounds wherein $R^1$ is hydrogen or methyl.

More particularly, the present invention provides such compounds wherein $R^2$ and $R^3$ are each independently a) hydrogen, b) —($C_1$–$C_4$)alkyl, c) —($C_3$–$C_6$)cycloalkyl; or d) phenyl optionally substituted with one or two substituents, each substituent is independently selected from 1)

—($C_1$–$C_4$)alkyl, 2) —($C_3$–$C_6$)cycloalkyl, 3) —O—($C_1$–$C_4$) alkyl, 4) fluoro or 5) chloro.

More particularly, the present invention provides such compounds wherein $R^2$ and $R^3$ are each independently hydrogen or methyl.

Even more particularly, the present invention provides such compounds wherein $R^2$ is hydrogen and $R^3$ is hydrogen.

Even more particularly, the present invention provides such compounds wherein $R^2$ is methyl and $R^3$ is methyl.

More particularly, the present invention provides such compounds of formula I wherein X is 1,3,5-triazin-2-yl having $R^{z1}$ and $R^{z2}$ substituents.

Even more particularly, the present invention provides such compounds wherein one of the $R^{z1}$ and $R^{z2}$ substituents is hydrogen and the other is methyl, cyclopropyl, —$CH_2OH$, —$CH(CH_3)OH$ or phenyl.

Even more particularly, the present invention provides such compounds wherein one of the $R^{z1}$ and $R^{z2}$ substituents is methyl and the other is methoxy or phenyl optionally substituted with 2-hydroxy.

Even more particularly, the present invention provides such compounds wherein one of the $R^{z1}$ and $R^{z2}$ substituents is hydroxy and the other is methyl or phenyl.

More particularly, the present invention provides such compounds of formula I wherein X is —$SO_2N(CH_3)_2$.

More particularly, the present invention provides such compounds of formula I wherein X is —C(=O)-benzofuranyl.

More particularly, the present invention provides such compounds of formula I wherein X is —C(=O)-furanopyridyl.

The present invention also provides pharmaceutical compositions comprising a compound of formula I, a prodrug thereof or a pharmaceutically acceptable salt of said compound or said prodrug and a pharmaceutically acceptable carrier or diluent.

The present invention also provides methods of inhibiting sorbitol dehydrogenase in a mammal in need of such inhibition comprising administering to said mammal a sorbitol dehydrogenase inhibiting amount of a compound of formula I, a prodrug thereof or a pharmaceutically acceptable salt of said compound or said prodrug.

The present invention also provides methods of treating diabetes in a mammal suffering from diabetes comprising administering to said mammal an effective amount of a compound of formula I, a prodrug thereof or a pharmaceutically acceptable salt of said compound or said prodrug.

The present invention also provides methods of treating diabetic complications in a mammal comprising administering to said mammal an effective amount of a compound of formula I, a prodrug thereof or a pharmaceutically acceptable salt of said compound or said prodrug. The present invention also provides such methods wherein said mammal is suffering from diabetes. The present invention also provides such methods wherein said diabetic complication is diabetic neuropathy. The present invention also provides such methods wherein said diabetic complication is diabetic nephropathy. The present invention also provides such methods wherein said diabetic complication is diabetic retinopathy. The present invention also provides such methods wherein said diabetic complication is foot ulcers. The present invention also provides such methods wherein said diabetic complication is a cardiovascular condition.

The combination aspects of the present invention include any and/or all of the following: the composition aspect of this invention wherein a composition comprises a first compound of formula I, a prodrug of said first compound or a pharmaceutically acceptable salt of said first compound or said prodrug, and a second compound, a prodrug thereof or a pharmaceutically acceptable salt of said second compound or said prodrug; the kit aspects of this invention; and, the therapeutic method aspect of this invention wherein the methods comprise administering a first compound of formula I, a prodrug of said first compound or a pharmaceutically acceptable salt of said first compound or said prodrug, and a second compound, a prodrug thereof or a pharmaceutically acceptable salt of said second compound or said prodrug.

Thus, the combination aspects of the present invention include, for example, pharmaceutical compositions comprising a compound of formula I, a prodrug thereof or a pharmaceutically acceptable salt of said compound or said prodrug, and a second compound selected from an aldose reductase inhibitor, a sodium hydrogen ion exchange (NHE-1) inhibitor, a glycogen phosphorylase inhibitor (GPI), a selective serotonin reuptake inhibitor, a 3-hydroxy-3-methylglutaryl coenzyme A reductase inhibitor, an angiotensin converting enzyme inhibitor, a thiazolidinedione antidiabetic agent, an angiotensin II receptor antagonist, a γ-aminobutyric acid (GABA) agonist, a phosphodiesterase type 5 inhibitor, an adenosine agonist, a CETP inhibitor, a prodrug thereof or a pharmaceutically acceptable salt of said second compound or said prodrug. The present invention also provides such compositions additionally comprising a pharmaceutically acceptable carrier or diluent.

The combination aspects of the present invention also include kits comprising: a.) a compound of formula I, a prodrug thereof or a pharmaceutically acceptable salt of said compound or said prodrug in a first unit dosage form; b.) an aldose reductase inhibitor, a sodium hydrogen ion exchange (NHE-1) inhibitor, a glycogen phosphorylase inhibitor (GPI), a selective serotonin reuptake inhibitor, a 3-hydroxy-3-methylglutaryl coenzyme A reductase inhibitor, an angiotensin converting enzyme inhibitor, a thiazolidinedione antidiabetic agent, an angiotensin II receptor antagonist, a γ-aminobutyric acid (GABA) agonist, a phosphodiesterase type 5 inhibitor, an adenosine agonist, a CETP inhibitor, a prodrug thereof or a pharmaceutically acceptable salt of said second compound or said prodrug, in a second unit dosage form; and c.) a container The combination aspects of the present invention also include methods of treating diabetic complications in a mammal comprising administering to said mammal an effective amount of a compound of formula I, a prodrug thereof or a pharmaceutically acceptable of said compound or said prodrug, and a second compound selected from an aldose reductase inhibitor, a sodium hydrogen ion exchange (NHE-1) inhibitor, a glycogen phosphorylase inhibitor (GPI), a selective serotonin reuptake inhibitor, a 3-hydroxy-3-methylglutaryl coenzyme A reductase inhibitor, an angiotensin converting enzyme inhibitor, a thiazolidinedione antidiabetic agent, an angiotensin II receptor antagonist, a γ-aminobutyric acid (GABA) agonist, a phosphodiesterase type 5 inhibitor, an adenosine agonist, a CETP inhibitor, a prodrug thereof or a pharmaceutically acceptable salt of said second compound or said prodrug. The present invention also provides such methods wherein said mammal is suffering from diabetes. The present invention also provides such methods wherein said diabetic complication is diabetic neuropathy. The present invention also provides such methods wherein said diabetic complication is diabetic nephropathy. The present invention also provides such methods wherein said diabetic complication is diabetic retinopathy. The present invention also provides such methods wherein said diabetic complication is foot ulcers. The present invention also provides such methods wherein said diabetic complication is a cardiovascular condition.

In a preferred embodiment of the combination aspects of the present invention, the second compound comprises an aldose reductase inhibitor, preferably in an aldose reductase inhibiting amount.

In an additional preferred embodiment of the combination aspects of the present invention, the second compound comprises a sodium hydrogen ion exchange (NHE-1) inhibitor, preferably in a NHE-1 inhibiting amount.

In an additional preferred embodiment of the combination aspects of the present invention, the second compound comprises a glycogen phosphorylase inhibitor, preferably in a glycogen phosphorylase inhibiting amount.

In a further preferred embodiment of the combination aspects of the present invention, the second compound comprises a selective serotonin reuptake inhibitor, preferably in a selective serotonin reuptake inhibiting amount.

In a further preferred embodiment of the combination aspects of the present invention, the second compound comprises a 3-hydroxy-3-methylglutaryl coenzyme A reductase inhibitor, preferably in a 3-hydroxy-3-methylglutaryl coenzyme A reductase inhibiting amount.

In another preferred embodiment of the combination aspects of the present invention, the second compound comprises an angiotensin converting enzyme inhibitor, preferably in an angiotensin converting enzyme inhibiting amount.

In a further preferred embodiment of the combination aspects of the present invention, the second compound comprises a thiazolidinedione antidiabetic agent, preferably in an insulin sensitivity increasing amount.

In another preferred embodiment of the combination aspects of the present invention, the second compound comprises an angiotensin II receptor antagonist, preferably in an angiotensin II receptor blocking amount.

In a further preferred embodiment of the combination aspects of the present invention, the second compound comprises a γ-aminobutyric acid (GABA) agonist, preferably in a γ-aminobutyric acid receptor binding amount.

In an additional preferred embodiment of the combination aspects of the present invention, the second compound comprises a phosphodiesterase type 5 inhibitor, preferably in a phosphodiesterase type 5 inhibiting amount.

In an additional preferred embodiment of the combination aspects of the present invention, the second compound comprises an adenosine agonist, preferably in an adenosine agonistic amount.

In an additional preferred embodiment of the combination aspects of the present invention, the second compound comprises a CETP inhibitor, preferably in a CETP inhibitory amount.

A further preferred embodiment of the combination aspects of the present invention includes methods of treating diabetes in a mammal suffering from diabetes comprising administering to said mammal an effective amount of a compound of formula I, a prodrug thereof or a pharmaceutically acceptable salt of said compound or said prodrug and an aldose reductase inhibitor, a prodrug of said aldose reductase inhibitor or a pharmaceutically acceptable salt of said aldose reductase inhibitor or said prodrug.

Another preferred embodiment of the combination aspect of the present invention provides methods of treating diabetes in a mammal suffering from diabetes comprising administering to said mammal an effective amount of a compound of formula I, a prodrug thereof or a pharmaceutically acceptable salt of said compound or said prodrug, and a sodium hydrogen ion exchange (NHE-1) inhibitor, a prodrug of said NHE-1 inhibitor or a pharmaceutically acceptable salt of said NHE-1 inhibitor or said prodrug.

Another preferred embodiment of the combination aspect of the present invention provides methods of treating diabetes in a mammal comprising administering to said mammal a compound of formula I, a prodrug thereof or a pharmaceutically acceptable salt of said compound or said prodrug and a glycogen phosphorylase inhibitor (GPI), a prodrug of said GPI or a pharmaceutically acceptable salt of said GPI or said prodrug.

A further preferred embodiment of the combination aspects of the present invention includes methods of treating hyperglycemia in a mammal comprising administering to said mammal a compound of formula I, a prodrug thereof or a pharmaceutically acceptable salt of said compound or said prodrug and a glycogen phosphorylase inhibitor (GPI), a prodrug of said GPI or a pharmaceutically acceptable salt of said GPI or said prodrug.

A further preferred embodiment of the combination aspects of the present invention includes methods of treating ischemia in a mammal comprising adminstering to said mammal a compound of formula I, a prodrug thereof or a pharmaceutically acceptable salt of said compound or said prodrug and a glycogen phosphorylase inhibitor (GPI), a prodrug of said GPI or a pharmaceutically acceptable salt of said GPI or said prodrug.

Another preferred embodiment of the combination aspect of the present invention provides methods of treating ischemia in a mammal suffering from ischemia comprising administering to said mammal an effective amount of a compound of formula I, a prodrug thereof or a pharmaceutically acceptable salt of said compound or said prodrug and a sodium hydrogen ion exchange (NHE-1) inhibitor, a prodrug of said NHE-1 inhibitor or a pharmaceutically acceptable salt of said NHE-1 inhibitor or said prodrug. The present invention also provides such methods wherein said ischemia is perioperative myocardial ischemia.

In addition, the present invention provides methods of reducing tissue damage resulting from ischemia comprising administering to a mammal in need of said treatment an effective amount of a compound of formula I, a prodrug thereof or a pharmaceutically acceptable salt of said compound or said prodrug; wherein said ischemia is a result of an etiology independent of diabetic microangiopathy or diabetic macroangiopathy. The present invention provides such methods wherein the tissue is heart, brain, liver, kidney, lung, gut, skeletal muscle, spleen, pancreas, retina or intestinal tissue.

In addition, the present invention provides methods of providing a cardioprotective effect in a mammal which comprises administering to the mammal an effective amount of a compound of formula I, a prodrug thereof or a pharmaceutically acceptable salt of said compound or said prodrug.

Also, the present invention provides processes for preparing a compound of formula 3-8C

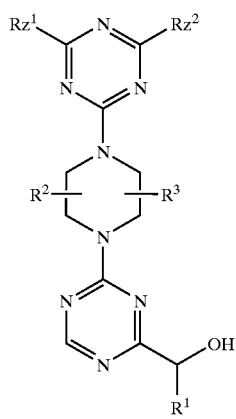

wherein the variables are as defined above;

which comprises the steps of:

a) reacting a compound of formula 3-5

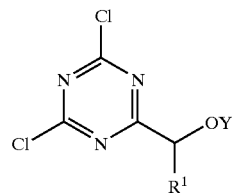

3-5 wherein Y is a) —(C$_1$–C$_4$)alkyl, b) —C(O)—(C$_1$–C$_4$)alkyl-N—((C$_1$–C$_4$)alkyl)$_2$, c) —C(O)—(C$_1$–C$_4$)alkyl, d) —C(O)-phenyl or e) —CH$_2$-phenyl; wherein each occurrence of phenyl is optionally substituted with one or two substituents, each independently selected from —(C$_1$–C$_4$)alkyl, —O—(C$_1$–C$_4$)alkyl, fluoro or chloro; and wherein R$^1$ is as defined above; with an R$^2$- and R$^3$-substituted piperazine wherein R$^2$ and R$^3$ are as defined above; in a reaction inert solvent and in the presence of a tertiary amine base to obtain a compound of formula 3-7

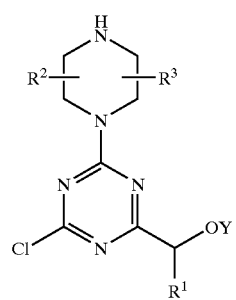

3-7 wherein the variables are as defined above;

b) reacting the compound of formula 3-7 with a compound of formula 3-8

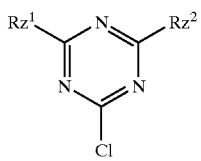

3-8 wherein the variables are as defined above; to obtain a compound of formula 3-8A

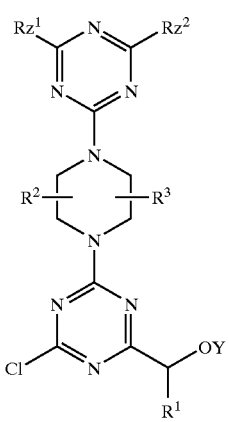

3-8A wherein the variables are as defined above;

c) dechlorinating the compound of formula 3-8A to obtain a compound of formula 3-8B

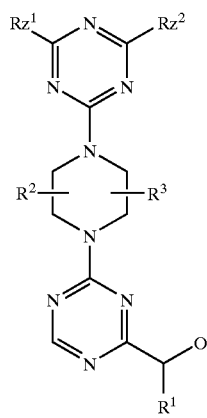

3-8B wherein the variables are as defined above; and d) deprotecting the compound of formula 3-8B to obtain a compound of formula 3-8C

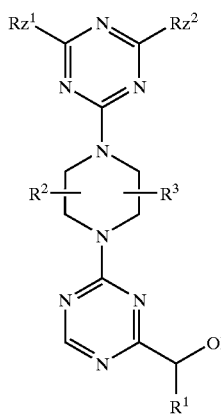

3-8C wherein the variables are as defined above.

The present invention also provides compounds selected from the group consisting of:
2,4-dichloro-6-(1-methoxyethyl)-[1,3,5]triazine; and
2,4-dichloro-6-(1-benzyloxyethyl)-[1,3,5]triazine.

The present invention also provides the following compounds:
compounds of formula 3-7

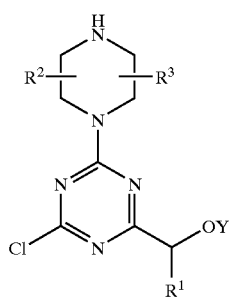

3-7 wherein Y is a) —(C$_1$-C$_4$)alkyl, b) —C(O)—(C$_1$-C$_4$)alkyl-N—((C$_1$-C$_4$)alkyl)$_2$, c) —C(O)—(C$_1$-C$_4$)alkyl, d) —C(O)-phenyl or e) —CH$_2$-phenyl; wherein each occurrence of phenyl is optionally substituted with one or two substituents, each independently selected from —(C$_1$-C$_4$)alkyl, —O—(C$_1$-C$_4$)alkyl, fluoro or chloro; and the other variables are as defined above;
compounds of formula 3-8A

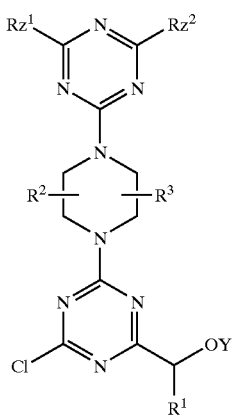

3-8A wherein Y is a) —(C$_1$-C$_4$)alkyl, b) —C(O)—(C$_1$-C$_4$)alkyl-N—((C$_1$-C$_4$)alkyl)$_2$, c) —C(O)—(C$_1$-C$_4$)alkyl, d) —C(O)-phenyl or e) —CH$_2$-phenyl; wherein each occurrence of phenyl is optionally substituted with one or two substituents, each independently selected from —(C$_1$-C$_4$)alkyl, —O—(C$_1$-C$_4$)alkyl, fluoro or chloro; and the other variables are as defined above; and
compounds of formula 3-8B

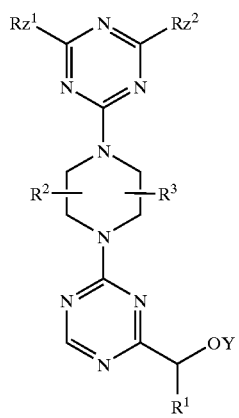

3-8B wherein Y is a) —(C$_1$-C$_4$)alkyl, b) —C(O)—(C$_1$-C$_4$)alkyl-N—((C$_1$-C$_4$)alkyl)$_2$, c) —C(O)—(C$_1$-C$_4$)alkyl, d) —C(O)-phenyl or e) —CH$_2$-phenyl; wherein each occurrence of phenyl is optionally substituted with one or two substituents, each independently selected from —(C$_1$-C$_4$)alkyl, —O—(C$_1$-C$_4$)alkyl, fluoro or chloro; and the other variables are as defined above.

The expressions "compound(s) of formula I" and "compound(s) of the present invention" as used herein, means a compound or compounds of formula I, isomer(s) thereof, prodrug(s) of said compound(s) or isomer(s), and pharmaceutically acceptable salt(s) of said compound(s), isomer(s) or prodrug(s). The term "compound(s)," when referring to compounds of formula I, also includes isomer(s) of said compound(s), prodrug(s) of said compound(s) or isomer(s), and pharmaceutically acceptable salt(s) of said compound(s), isomer(s) or prodrug(s).

The subject invention also includes isotopically-labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, $^{135}$I, and $^{36}$Cl, respectively Compounds of the present invention, which contain the aforementioned isotopes and/or other isotopes of other atoms, are within the scope of the present invention. Certain isotopically-labeled compounds of the present invention, for example, those into which radioactive isotopes such as $^3$H or $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, may afford certain therapeutic advantages resulting from greater metabolic stability, for example increased in vivo half-life or reduced dosage requirements and, hence, may be preferred in some circumstances. Isotopically labeled compounds of formula I of the present invention can generally be prepared by carrying out the procedures disclosed in the Schemes and/or in the Examples below, by substituting a readily available isotopically labeled reagent for a non-isotopically labeled reagent.

The term "reduction" is intended to include, in addition to substantially total prevention, partial prevention or prevention which, although greater than that which would result from taking no compound or from taking a placebo, is less than 100%.

The term "damage resulting from ischemia" as employed herein refers to conditions directly associated with reduced blood flow to tissue, for example, due to a clot or obstruction of blood vessels which supply blood to the subject tissue and which result, inter alia, in lowered oxygen transport to such tissue, impaired tissue performance, tissue dysfunction and/or necrosis. Alternatively, where blood flow or organ perfusion may be quantitatively adequate, the oxygen carrying capacity of the blood or organ perfusion medium may be reduced, e.g., in an hypoxic environment, such that oxygen supply to the tissue is lowered, and impaired tissue performance, tissue dysfunction, and/or tissue necrosis ensues.

The term "treating", "treat" or "treatment" as used herein includes preventative (e.g., prophylactic) and palliative treatment.

The term "pharmaceutically acceptable" means the carrier, diluent, excipient, and/or salt must be compatible with the other ingredients of the formulation, and not deleterious to the recipient thereof.

The term "effective amount" means an amount of a compound or combination of compounds that ameliorates, attenuates or eliminates a particular disease or condition or a symptom of a particular disease or condition, or prevents or delays the onset of a particular disease or condition or a symptom of a particular disease or condition.

The expression "prodrug" refers to a compound that is a drug precursor which following administration, releases the drug in vivo via some chemical or physiological process (e.g., a prodrug on being brought to the physiological pH or through enzyme action is converted to the desired drug form). Prodrugs of the compounds of the present invention include, e.g., derivatives of the hydroxyl group in the compound of formula I wherein H is replaced by —($C_1$–$C_4$) alkyl, —C(O)—($C_1$–$C_4$)alkyl-N—($C_1$–$C_4$ alkyl)$_2$, —C(O)—($C_1$–$C_4$)alkyl, —C(O)-phenyl, —CH$_2$-phenyl in which the phenyl ring is optionally substituted with one or two substituents selected from, e.g., —($C_1$–$C_4$)alkyl, fluoro, chloro or —O—($C_1$–$C_4$)alkyl.

This invention is further directed to compounds which are mutual prodrugs of aldose reductase inhibitors and sorbitol dehydrogenase inhibitors. By mutual prodrug is meant a compound which contains two active components, in this case, an aldose reductase inhibitor and a sorbitol dehydrogenase inhibitor, which, following administration, is cleaved, releasing each individual active component. Such mutual prodrugs of an aldose reductase inhibitor and a sorbitol dehydrogenase inhibitor are formed under standard esterification conditions well known to those skilled in the art. For example, mutual prodrugs of the compounds of the present invention and an aldose reductase inhibitor would include compounds of formula I wherein the hydrogen atom of the hydroxy group, which appears in formula I, is replaced with an acyl radical of a carboxylic acid aldose reductase inhibitor. Examples of carboxylic acid aldose reductase inhibitors would include ponalrestat, tolrestat, zenarastat, zopolrestat and epalrestat.

By alkylene is meant an unsaturated hydrocarbon (straight chain or branched) wherein a hydrogen atom is removed from each of the terminal carbons. Exemplary of such groups (assuming the designated length encompasses the particular example) are methylene, ethylene, propylene, butylene, pentylene, hexylene and heptylene.

By halo is meant fluoro, chloro, bromo or iodo.

By alkyl is meant a saturated hydrocarbon (straight chain or branched). Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By cycloalkyl is meant a cyclic hydrocarbon. Examples of cycloalkyl groups include cyclopropyl, cyclobutyl, cyclopentyl, cyclohexyl and cycloheptyl. Preferred cycloalkyl groups are ($C_3$–$C_6$)cycloalkyl.

By alkoxy is meant saturated alkyl (straight chain or branched) bonded through an oxygen. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

The term "substituted" when used to describe a phenyl or naphthyl ring, refers to replacement of a hydrogen atom of the phenyl or naphthyl ring with another atom or group of atoms. For example, the term "mono-substituted" means that only one of the hydrogens of the phenyl or naphthyl ring has been substituted. The term "di-substituted" means that two of the hydrogens of the phenyl or naphthyl ring have been substituted.

It is to be understood that if a carbocyclic or heterocyclic moiety may be bonded or otherwise attached to a designated substrate through differing ring atoms without denoting a specific point of attachment, then all possible points of attachment are intended, whether through a carbon atom or, for example, a trivalent nitrogen atom. For example, the term "pyridyl" means 2-, 3- or 4-pyridyl; the term "thienyl" means 2- or 3-thienyl, and so forth.

The expression "pharmaceutically acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. Where more than one basic moiety exists the expression includes multiple salts (e.g., di-salt). The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

As used herein, the expressions "reaction inert solvent" and "inert solvent" refer to a solvent or mixture of solvents which does not interact with starting materials, reagents, intermediates or products in a manner which adversely affects the yield of the desired product.

The chemist of ordinary skill in the art will recognize that certain compounds of formula I of this invention will contain one or more atoms which may be in a particular stereochemical or geometric configuration, giving rise to stereoisomers and configurational isomers. All such isomers and mixtures thereof are included in this invention. Compounds of formula I may be chiral. In such cases, the isomer wherein the asymmetric carbon atom attached to $R^1$ has the R configuration is preferred.

Those skilled in the art will further recognize that the compounds of formula I can exist in crystalline form as hydrates wherein molecules of water are incorporated within the crystal structure thereof and as solvates wherein molecules of a solvent are incorporated therein. All such hydrate and solvate forms are considered part of this invention.

The chemist of ordinary skill in the art will also recognize that certain compounds of formula I of this invention can exist in tautomeric form, i.e., that an equilibrium exists between two isomers which are in rapid equilibrium with each other. A common example of tautomerism is keto-enol tautomerism, i.e.,

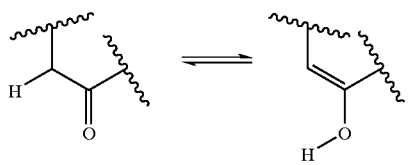

Examples of compounds which can exist as tautomers include hydroxypyridines, hydroxypyrmidines, hydroxyquinolines and hydroxytriazines. Other examples will be recognized by those skilled in the art. All such tautomers and mixtures thereof are included in this invention.

DMF means N,N-dimethylformamide. DMSO means dimethyl sulfoxide. THF means tetrahydrofuran.

Whenever the structure of a cyclic radical is shown with a bond drawn from outside the ring to inside the ring, it will be understood by those of ordinary skill in the art to mean that the bond may be attached to any atom on the ring with an available site for bonding. If the cyclic radical is a bicyclic or tricyclic radical, then the bond may be attached to any atom on any of the rings with an available site for bonding. For example,

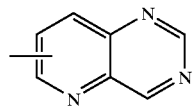

represents any or all of the following radicals:

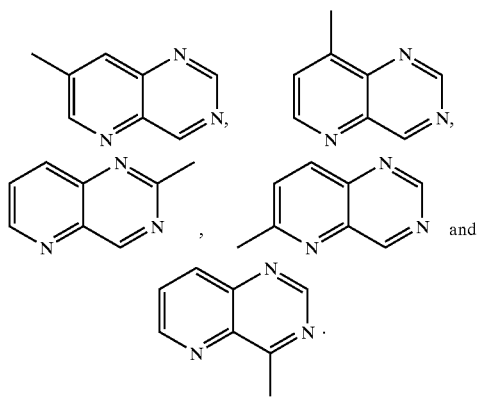

DETAILED DESCRIPTION OF THE INVENTION

In general, the compounds of formula I of the present invention can be made by processes analogous to those known in the chemical arts, particularly in light of the description contained herein. Certain processes for the preparation of the compounds of formula I of the present invention are provided as further features of the present invention and are illustrated by the following reaction schemes. Other processes are described in the experimental section.

The compounds of the present invention are prepared as described in the schemes below:

SCHEME 1

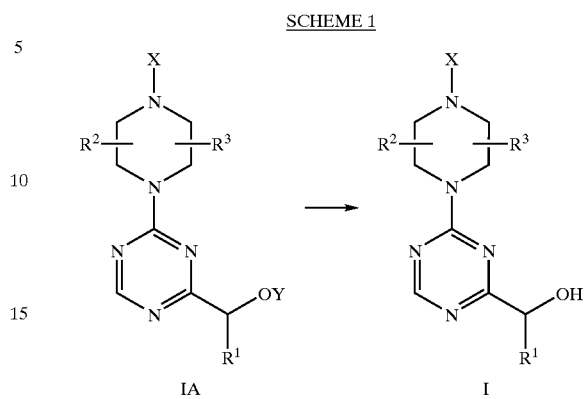

Scheme 1

Compounds of the present invention of formula I, wherein the variables are as defined in the Summary above, can be prepared from compounds of formula IA, wherein Y is, e.g., —($C_1$-$C_4$)alkyl, —C(O)—($C_1$-$C_4$)alkyl-N—(($C_1$-$C_4$)alkyl)$_2$, —C(O)—($C_1$-$C_4$)alkyl, —C(O)-phenyl (in which the phenyl ring is optionally substituted with one or two substituents, each independently selected from, e.g., —($C_1$-$C_4$)alkyl, fluoro, chloro or —O—($C_1$-$C_4$)alkyl) or —$CH_2$-phenyl (in which the phenyl moiety is optionally substituted with one or two substituents, each independently selected from, e.g., —($C_1$-$C_4$)alkyl, —O—($C_1$-$C_4$)alkyl, fluoro or chloro).

When Y is —($C_1$-$C_4$)alkyl, the compound of formula IA is reacted with boron tribromide in either chloroform or methylene chloride. The preferred solvent is methylene chloride. The reaction is usually conducted at temperatures which are between about −70° C. and about 0° C. When Y is —C(O)—($C_1$-$C_4$)alkyl, —C(O)—($C_1$-$C_4$)alkyl-N—(($C_1$-$C_4$)alkyl)$_2$ or —C(O)-phenyl in which the phenyl ring is optionally substituted as described above, the compound of formula IA is reacted with either aqueous sodium or potassium hydroxide or concentrated HCl. The reaction can be conducted in the presence of water-miscible organic solvents such as alcohols, dioxane or THF. Preferred cosolvents are ethanol, methanol or THF. The temperature of the reaction ranges from room temperature to about 80° C., and the preferred temperature is room temperature.

When Y is —$CH_2$-phenyl in which the phenyl moiety is optionally substituted as described above, the compound of formula IA is hydrogenated in the presence of platinum or palladium catalyst in an alcoholic solvent or acetic acid admixed with a small amount of a mineral acid, such as concentrated HCl or $H_2SO_4$. The preferred alcoholic solvent is ethanol. The reaction is conducted at room temperature and at ambient or pressures up to about 2.7 atm. Alternatively, when Y is —$CH_2$-phenyl, as described above, the compound of formula IA can be reacted with a palladium catalyst in an alcoholic solvent in the presence of HCl gas dissolved in ether. The preferred alcoholic solvent is isopropanol. The reaction is conducted at ambient pressure and the temperature ranges from room temperature to about 100° C.

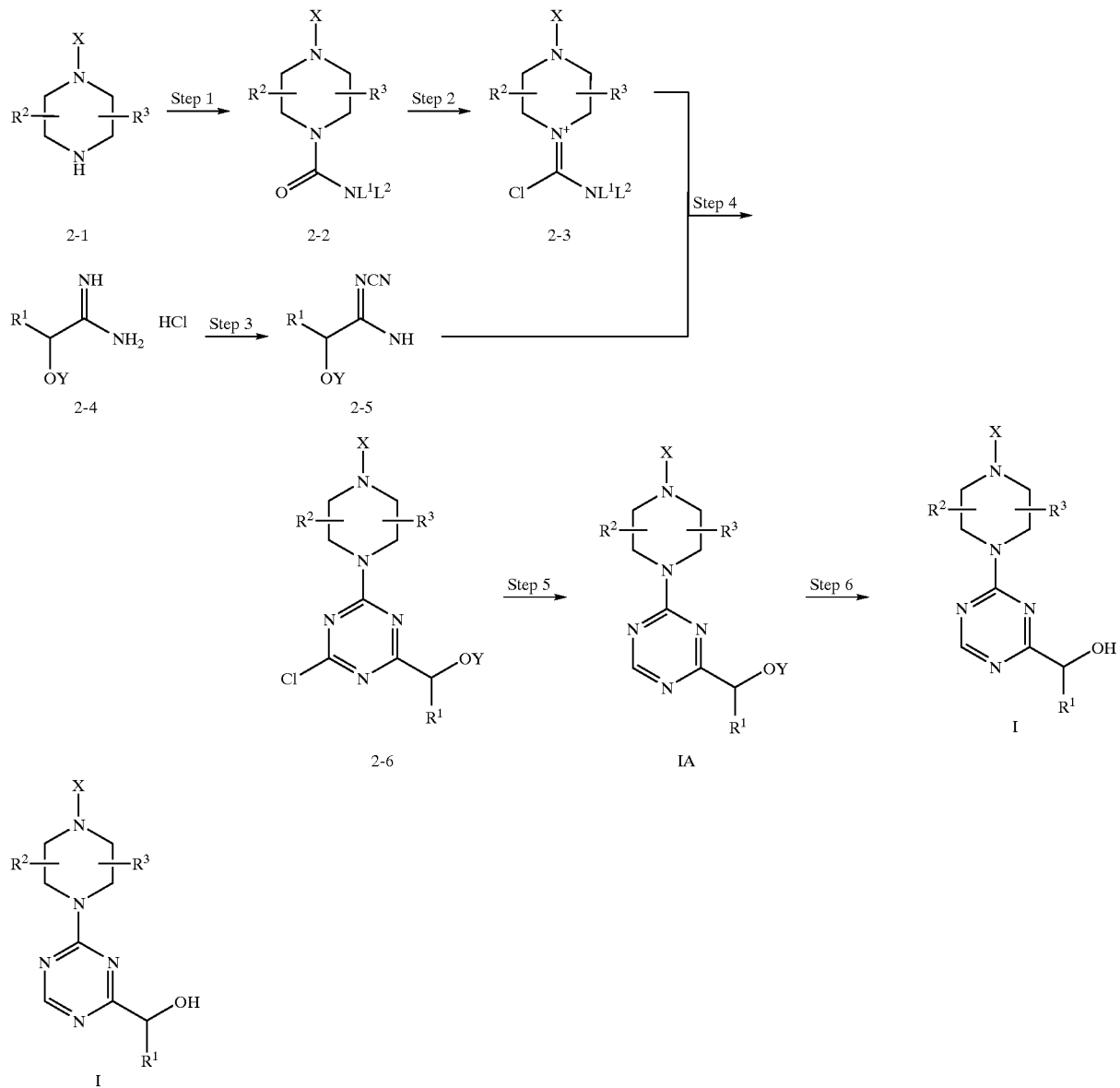

Scheme 2

In Scheme 2, compounds of formula I, wherein the variables are as defined in the Summary above, are obtained from the compounds of formula IA wherein Y is —($C_1$–$C_4$) alkyl or —$CH_2$-phenyl in which the phenyl moiety is optionally substituted with one or two substituents, each independently selected from, e.g., —($C_1$–$C_4$)alkyl, —O—($C_1$–$C_4$)alkyl, fluoro or chloro.

Compounds of formula 2-2, wherein $L^1$ and $L^2$ are the same or different and are —($C_1$–$C_4$)alkyl, are prepared by reacting compounds of formula 2-1, which are commerically available, with $L^1L^2NCOL^3$, in which $L^3$ is chloro, in ether or halocarbon solvents such as ether, THF, chloroform or methylene chloride. The preferred solvents are THF and methylene chloride. The reaction is conducted in the presence of a tertiary nitrogen base such as triethylamine, dimethylisopropylamine or pyridine. The reaction temperature is between room temperature and about 100° C. The preferred temperature is room temperature. Compounds of formula 2-3 are prepared by reacting compounds of formula 2-2 with phosphorus trichloride, phosphorus pentachloride or phosphorus oxychloride at a temperature which is between about 100° C. and about 150° C.

Compounds of formula 2-5 are obtained by reacting compounds of formula 2-4, which are commerically available or prepared as described in International Publication WO 00/59510, published 12 Oct. 2000, with cyanogen bromide in acetonitrile admixed with an alcoholic solvent such as ethanol or isopropanol. The preferred alcoholic solvent is ethanol. The reaction is conducted in the temperature range of about 0° C. to about 40° C. In Step 4 of Scheme 2, compounds of formula 2-3 are reacted with compounds of formula 2-5 in acetonitrile, according to the procedures set forth in *Synthesis*, 1980, 841–842, to give compounds of formula 2-6.

In Step 5 of Scheme 2, compounds of formula 2-6 are hydrogenated to remove the chlorine atom and to obtain compounds of formula IA. This reaction is conducted in the presence of hydrogen, either palladium or platinum catalyst, and an alcoholic solvent such as ethanol, containing sodium or potassium hydroxide. The reaction is conducted at high pressure in the range of about 2.7 to about 3.4 atm. In Step 6 of Scheme 2, the compounds of formula I are obtained from compounds of formula IA, according to procedures described in Scheme 1 above.

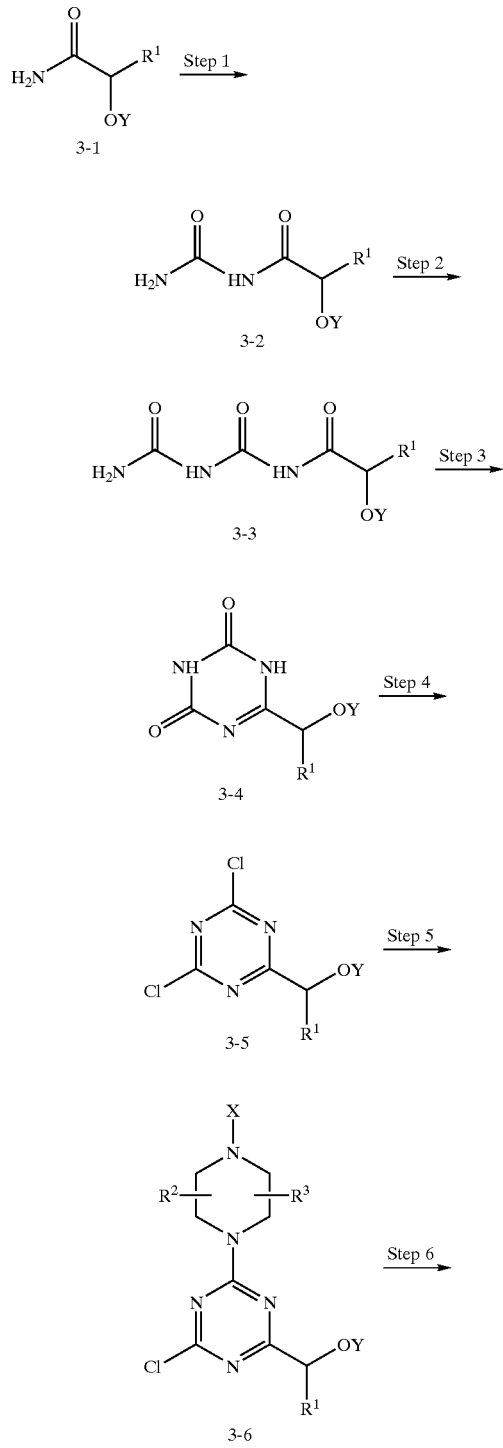

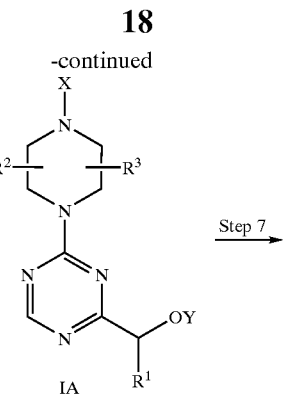

Scheme 3

Scheme 3 discloses alternative procedures for the preparation of compounds of formula I, wherein the variables are as defined in the Summary above, from the compounds of formula IA wherein Y is —($C_1$–$C_4$)alkyl or —$CH_2$-phenyl in which the phenyl moiety is optionally substituted with one or two substituents, each independently selected from, e.g., —($C_1$–$C_4$)alkyl, —O—($C_1$–$C_4$)alkyl, fluoro or chloro.

General procedures for the preparation of compounds of formula 3-1, wherein Y is defined above and $R^1$ is defined in the Summary above, are described in the literature, for example, Helv. Chim. Acta, 1971, 845–851. Compounds of formula 3-1 are reacted in Step 1 with chlorosulfonyl isocyanate to obtain compounds of formula 3-2. The reaction is conducted in a reaction-inert solvent such as ether, THF, diglyme or acetonitrile. The preferred solvent is acetonitrile. The range of the reaction temperature is between room temperature and about 60° C. The reaction is conducted at ambient pressure. Compounds of formula 3-2 are reacted in Step 2 with chlorosulfonyl isocyanate to obtain compounds of formula 3-3. The reaction is conducted in a reaction-inert solvent such as ether, THF, diglyme or acetonitrile. The preferred solvent is acetonitrile. The reaction temperature is between room temperature and about 60° C. The reaction is conducted at ambient pressure.

Compounds of formula 3-3 are cyclized in Step 3 to give compounds of formula 3-4, using either aqueous NaOH or KOH. The reaction is conducted at temperatures which are between about 0° C. and room temperature and at ambient pressure. Compounds of formula 3-5 are prepared in Step 4 by reacting compounds of formula 3-4 with $PCl_3$, $PCl_5$ or $POCl_3$ in the presence of a tertiary nitrogen base such as a trialkyl amine or a dialkyl aniline. The preferred conditions are POCl₃ in the presence of diethyl aniline. The reaction is usually conducted at temperatures which are between about 50° and about 100° C. and at ambient pressure. Step 5 involves the displacement of one of the chlorine atoms in the compounds of formula 3-5 by substituted piperazines having substituents R², R³ and X as described in the Summary above, in the presence of either an inorganic base, such as sodium or potassium bicarbonate or carbonate, or a tertiary nitrogen base, such as triethylamine, isopropylethylamine or diazabicyclononane, to obtain compounds of formula 3-6. The preferred bases are sodium or potassium bicarbonate. The reaction is conducted at ambient pressure, at temperatures which are between room temperature and about 60° C., and in a polar non-aqueous solvent, such as acetonitrile or DMF. The preferred temperature is room temperature and the preferred solvent is DMF.

In Step 6, compounds of formula 3-6 are hydrogenated to remove the chlorine atom to give the compounds of formula IA. This reaction is conducted in the presence of hydrogen, either palladium or platinum catalyst, and an alcoholic solvent, such as ethanol, containing sodium or potassium hydroxide. The reaction is conducted at a pressure in the range of about 2.7 to about 3.4 atm. In Step 7 of Scheme 3, the compounds of formula I are obtained from compounds of formula IA, according to procedures described in Scheme 1 above.

SCHEME 3A

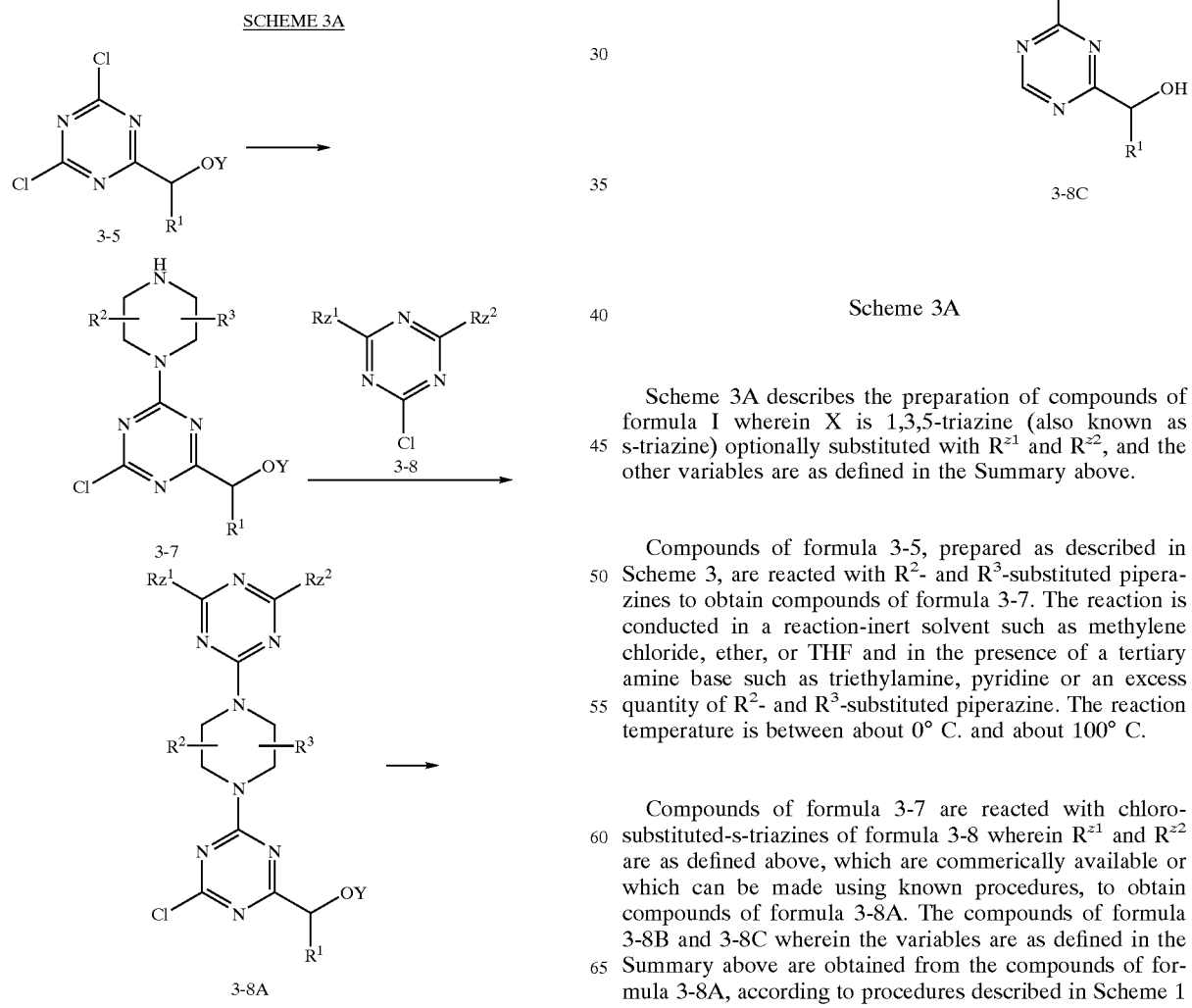

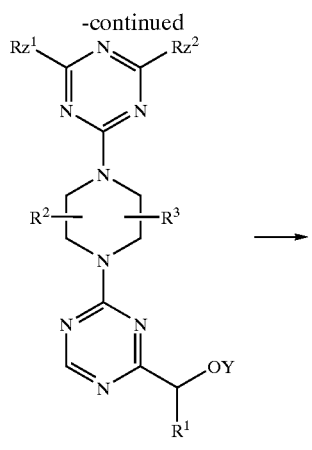

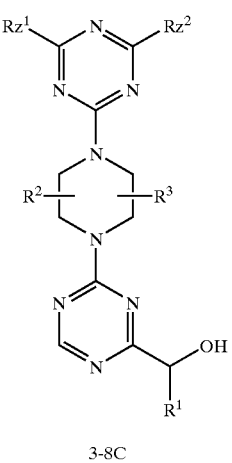

Scheme 3A

Scheme 3A describes the preparation of compounds of formula I wherein X is 1,3,5-triazine (also known as s-triazine) optionally substituted with $R^{z1}$ and $R^{z2}$, and the other variables are as defined in the Summary above.

Compounds of formula 3-5, prepared as described in Scheme 3, are reacted with R²- and R³-substituted piperazines to obtain compounds of formula 3-7. The reaction is conducted in a reaction-inert solvent such as methylene chloride, ether, or THF and in the presence of a tertiary amine base such as triethylamine, pyridine or an excess quantity of R²- and R³-substituted piperazine. The reaction temperature is between about 0° C. and about 100° C.

Compounds of formula 3-7 are reacted with chloro-substituted-s-triazines of formula 3-8 wherein $R^{z1}$ and $R^{z2}$ are as defined above, which are commerically available or which can be made using known procedures, to obtain compounds of formula 3-8A. The compounds of formula 3-8B and 3-8C wherein the variables are as defined in the Summary above are obtained from the compounds of formula 3-8A, according to procedures described in Scheme 1 above.

SCHEME 3B

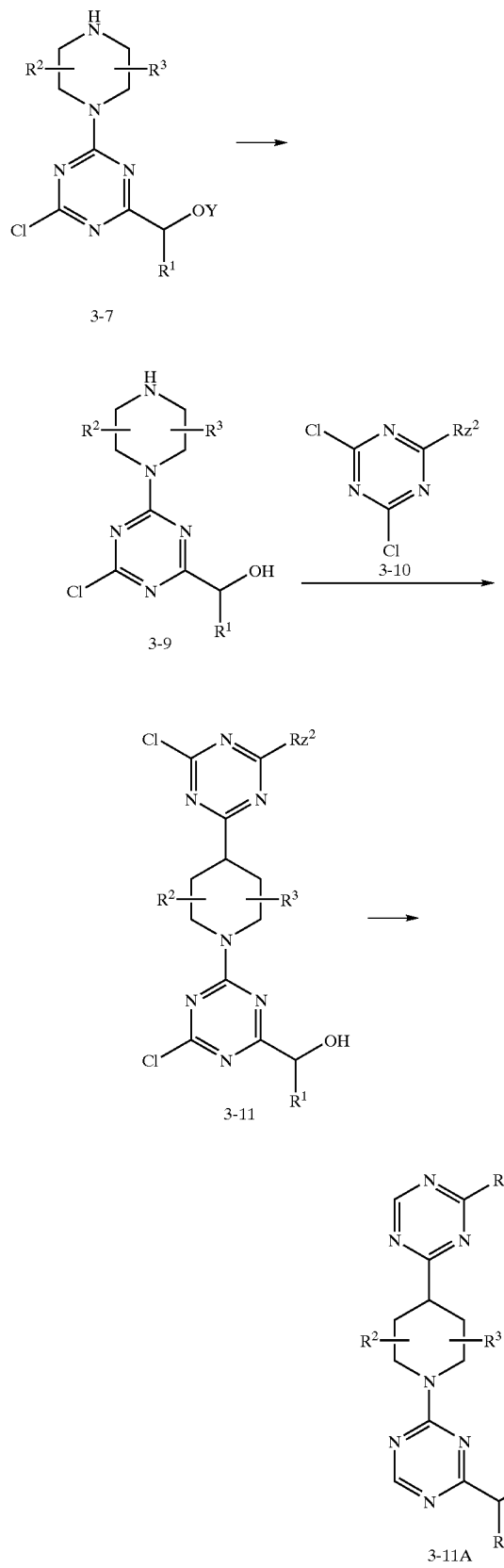

Compounds of formula I wherein X is s-triazine with one substituent $R^{z2}$, and the other variables are as defined in the Summary above, are prepared as described in Scheme 3B.

Compounds of formula 3-7, prepared as described in Scheme 3A, are reacted with boron tribromide in either chloroform or methylene chloride to give compounds of formula 3-9. The preferred solvent is methylene chloride. The reaction is usually conducted at temperatures which are between about −70° C. and about 0° C. Compounds of formula 3-9 are reacted with dichloro-substituted-s-triazine of formula 3-10, which are commercially available, to obtain compounds of formula 3-11. The reaction is conducted in the presence of a tertiary amine base, such as triethylamine, pyridine or excess compound of formula 3-7 in a reaction-inert solvent, such as methylene chloride, chloroform or THF.

Reductive removal of the chlorine atoms in the compounds of formula 3-11 completes the sequence of steps to obtain the compounds of formula 3-11 A wherein the variables are as defined in the Summary above. The reaction is catalyzed by palladium or platinum catalysts, in a Parr hydrogenator at pressures in the range of about 3.1 to about 3.7 atm and at room temperature. Solvents for the reaction are alcoholic solvents and the preferred alcohol is isopropanol.

SCHEME 3C

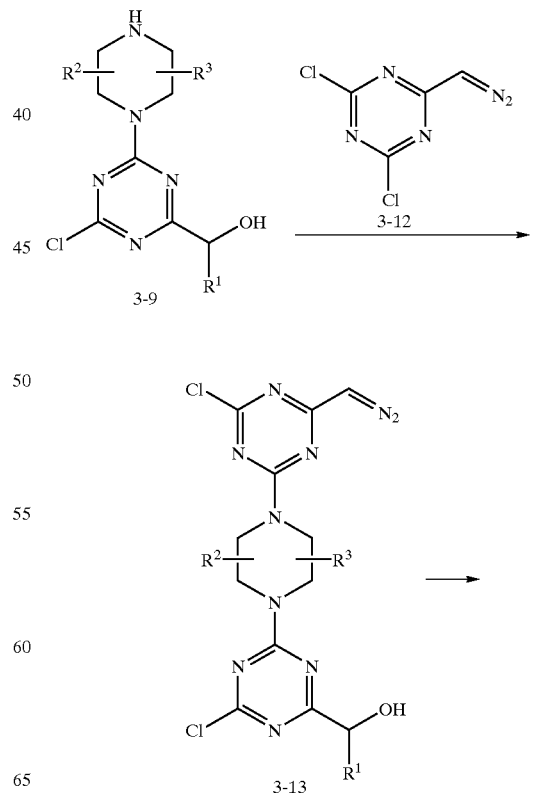

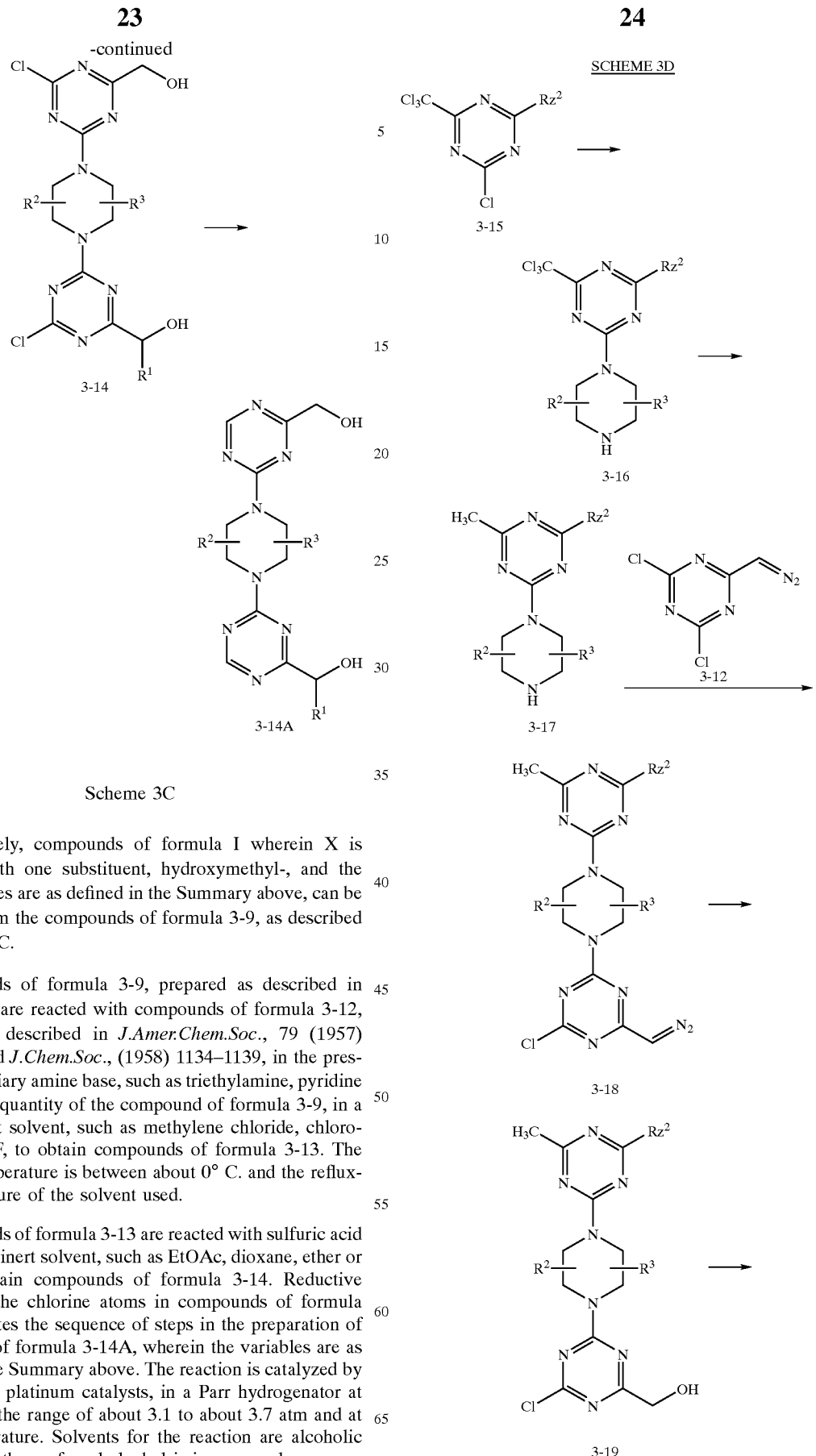

Scheme 3C

Alternatively, compounds of formula I wherein X is s-triazine with one substituent, hydroxymethyl-, and the other variables are as defined in the Summary above, can be prepared from the compounds of formula 3-9, as described in Scheme 3C.

Compounds of formula 3-9, prepared as described in Scheme 3B, are reacted with compounds of formula 3-12, prepared as described in J.Amer.Chem.Soc., 79 (1957) 944–948, and J.Chem.Soc., (1958) 1134–1139, in the presence of a tertiary amine base, such as triethylamine, pyridine or an excess quantity of the compound of formula 3-9, in a reaction-inert solvent, such as methylene chloride, chloroform or THF, to obtain compounds of formula 3-13. The reaction temperature is between about 0° C. and the refluxing temperature of the solvent used.

Compounds of formula 3-13 are reacted with sulfuric acid in a reaction-inert solvent, such as EtOAc, dioxane, ether or THF, to obtain compounds of formula 3-14. Reductive removal of the chlorine atoms in compounds of formula 3-14 completes the sequence of steps in the preparation of compounds of formula 3-14A, wherein the variables are as defined in the Summary above. The reaction is catalyzed by palladium or platinum catalysts, in a Parr hydrogenator at pressures in the range of about 3.1 to about 3.7 atm and at room temperature. Solvents for the reaction are alcoholic solvents and the preferred alcohol is isopropanol.

-continued

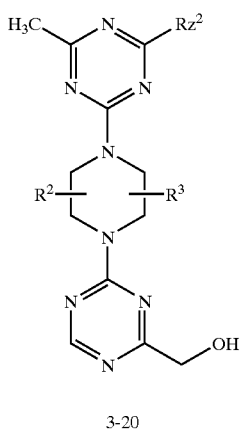

3-20

Scheme 3D

Alternatively, compounds of formula I, wherein $R^1$ is hydrogen, $R^2$ and $R^3$ are as described in the Summary above, and X is s-triazine having substituents $R^{z1}$ and $R^{z2}$, can be prepared according to the procedures set forth in Scheme 3D. For example, compounds of formula I, wherein X is s-triazine, $R^{z1}$ is methyl and $R^{z2}$ is phenyl optionally substituted as described in the Summary above, can also be prepared by procedures set forth in Scheme 3D.

Compounds of formula 3-15 are prepared by reacting $R^{z2}$—CN with trichloroacetonitrile and aluminum bromide in the presence of HCl gas. The reaction is conducted at temperatures which are between about 0° C. and about 20° C. and at ambient pressure. Compounds of formula 3-16 are prepared by reacting compounds of formula 3-15 with piperazines having $R^2$ and $R^3$ substituents as defined in the Summary above. The reaction is conducted in a reaction-inert solvent, such as methylene chloride, ether or THF, and in the presence of a tertiary amine base, such as triethylamine, pyridine or an excess quantity of $R^2$ and $R^3$-substituted piperazine. The reaction temperature is between about 0° C. and about 100° C.

Compounds of formula 3-17 are prepared by hydrogenating compounds of formula 3-16 to remove the chlorine atoms. This reaction is conducted in the presence of hydrogen, either palladium or platinum catalysts, and an alcoholic solvent, such as ethanol, containing sodium or potassium hydroxide. The reaction is conducted at a pressure in the range of about 2.7 to about 3.4 atm. Compounds of formula 3-18 are prepared by reacting compounds of formula 3-17 with 2,4-dichloro-6-diazomethyl-triazine, the compound of formula 3-12, which is also used in Scheme 3C above. This reaction is conducted in a reaction-inert solvent, such as methylene chloride, ether or THF, and in the presence of a tertiary amine base, such as triethylamine or pyridine. The reaction temperature is between about 0° C. and about 100° C.

Compounds of formula 3-19 are prepared by reacting compounds of formula 3-18 with sulfuric acid in the presence of a reaction-inert solvent, such as ethyl acetate, ether or THF. The reaction temperature is between about 0° C. and about 100° C. Compounds of formula 3-19 are transformed to compounds of formula 3-20 by removing the chlorine atoms through hydrogenation mediated by catalysts, such as palladium or platinum, in the presence of sodium or potassium hydroxide. The reaction is conducted at a pressure in the range of about 2.7 to about 3.4 atm and under standard reaction conditions.

SCHEME 3E

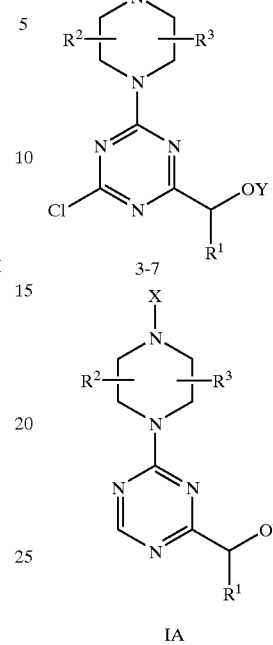

3-7

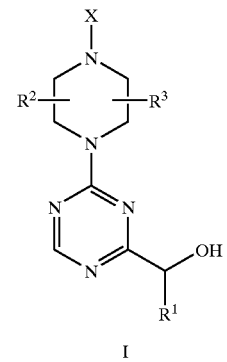

IA          I

Scheme 3E

Compounds of formula I wherein $R^1$, $R^2$ and $R^3$ are as described in the Summary above and X is —C(O)—$R^4$-Z, —$SO_2$—$R^4$-Z, —C(O)—$NR^5R^6$ or —$SO_2$—$NR^5R^6$, are prepared as described in Scheme 3E.

Compounds of formula 3-7, prepared as described in Scheme 3A, are reacted with $L^4$-C(O)—$R^4$-Z, $L^4$-$SO_2$—$R^4$-Z, $L^4$-CO—$NR^5R^6$ or $L^4$-$SO_2$—$NR^5R^6$, wherein $L^4$ is, e.g., chloro and the variables are as defined in the Summary above, in the presence of a tertiary amine base, such as triethylamine, pyridine or an excess quantity of the compound of formula 3-7, in a reaction-inert solvent, such as methylene chloride, chloroform or THF, to give the compound of formula IA. The reaction temperature is between about 0° C. and the refluxing temperature of the solvent used. The compounds of formula I are obtained from compounds of formula IA, according to procedures described in Scheme 1 above.

The starting materials and reagents for the above described compounds are also readily available or can be easily synthesized by those skilled in the art using conventional methods of organic synthesis. For example, many of the compounds used herein are related to, or are derived from, compounds found in nature, in which there is great scientific interest and commercial need, and accordingly many such compounds are commercially available or are reported in the literature or are easily prepared from other commonly available substances by methods which are reported in the literature.

The compounds of the present invention inhibit the enzyme activity of sorbitol dehydrogenase and as such have utility in the treatment of diabetic complications including, but not limited to, complications such as diabetic nephropathy, diabetic neuropathy, diabetic retinopathy, diabetic microangiopathy, diabetic macroangiopathy, diabetic cardiomyopathy and foot ulcers, in mammals. The compounds of the present invention also have utility in providing a cardioprotective effect in mammals.

The utility of the compounds of the present invention as medical agents in the treatment of diseases, such as are detailed herein, in mammals (e.g., humans) is demonstrated by the activity of the compounds of formula I of this invention in conventional assays. Such assays also provide a means whereby the activities of the compounds of formula I of the present invention can be compared with the activities of other known compounds. The results of these comparisons are useful for determining dosage levels in mammals, including humans, for the treatment of such diseases.

Measurement of SDH Activity

Male Sprague-Dawley rats (200–250 g) are used for these experiments. Diabetes is induced in some of the rats by a tail vein injection of streptozocin, 85 mg/kg. Twenty-four hours later, 4 groups of diabetic rats are given a single dose of the test compound (0.001 to 100 mg/kg) by oral gavage. Animals are sacrificed 4–6 hours after dosing and blood and sciatic nerves are harvested. Tissues and cells are extracted with 6% perchloric acid.

Sorbitol in erythrocytes and nerves is measured by a modification of the method of R. S. Clements et al. (*Science*, 166: 1007–8, 1969). Aliquots of tissue extracts are added to an assay system which has final concentrations of reagents of 0.033 M glycine, pH 9.4, 800 mM B-nicotine adenine dinucleotide, and 4 units/ml of sorbitol dehydrogenase. After incubation for 30 minutes at room temperature, sample fluorescence is determined on a fluorescence spectrophotometer with excitation at 366 nm and emission at 452 nm. After subtracting appropriate blanks, the amount of sorbitol in each sample is determined from a linear regression of sorbitol standards processed in the same manner as the tissue extracts.

Fructose is determined by a modification of the method described by M. Ameyama, *Methods in Enzymology*, 89: 20–25 (1982). Resazurin is substituted for ferricyamide. Aliquots of tissue extracts are added to the assay system, which has final concentrations of reagents of 1.2 M citric acid, pH 4.5, 13 mM resazurin, 3.3 units/ml of fructose dehydrogenase and 0.068% Triton X-100. After incubation for 60 minutes at room temperature, sample fluorescence is determined on a fluorescence spectrophotometer with excitation at 560 nm and emission at 580 nm. After subtracting appropriate blanks, the amount of fructose in each sample is determined from a linear regression of fructose standards processed in the same manner as the tissue extracts.

SDH activity is measured by a modification of the method described by U. Gerlach, *Methodology of Enzymatic Analyses*, edited by H. U. Bergmeyer, 3, 112–117 (1983). Aliquots of sera or urine are added to the assay system, which has final concentrations of reagents of 0.1 M potassium phosphate buffer, pH 7.4, 5 mM NAD, 20 mM sorbitol, and 0.7 units/ml of sorbitol dehydrogenase. After incubation for 10 minutes at room temperature, the average change in sample absorbance is determined at 340 nm. SDH activity is presented as milliOD$_{340}$ units/minute (OD$_{340}$=optical density at 340 nm).

The activity and thus utility of the compounds of the present invention as medical agents in providing protection from ischemic damage to tissue in a mammal can be demonstrated by the activity of the compounds in the in vitro assay described below and in U.S. Pat. No. 5,932,581, which is hereby incorporated by reference herein. This assay is more particularly directed to providing protection from ischemic damage to myocardial tissue (e.g., for inducing cardioprotection). The assay also provides a means whereby the activities of the compounds of the present invention can be compared with the activities of other known compounds. The results of these comparisons are useful for determining dosage levels in mammals, including humans, for inducing protection from ischemia, particularly in the myocardium.

Cardioprotection, as indicated by a reduction in infarcted myocardium, can be induced pharmacologically using adenosine receptor agonists in isolated, retrogradely perfused rabbit hearts as an in vitro model of myocardial ischemic preconditioning (Liu et al., Cardiovasc. Res., 28:1057–1061, 1994; and Tracey et al., Cardiovasc. Res., 28:410–415, 1997). The in vitro test described below demonstrates that a test compound (i.e., a compound of formula I of the present invention) can also pharmacologically induce cardioprotection, i.e., reduced myocardial infarct size, when administered to a rabbit isolated heart. The effects of the test compound are compared to ischemic preconditioning and the A1/A3 adenosine agonist, APNEA (N$^6$-[2-(4-aminophenyl)ethyl]adenosine), that has been shown to pharmacologically induce cardioprotection in the rabbit isolated heart (Liu et al., Cardiovasc. Res., 28:1057–1061, 1994). The exact methodology is described below:

The protocol used for these experiments closely follows that described by Liu et al., Cardiovasc. Res., 28:1057–1061, 1994. Male New Zealand White rabbits (3–4 kg) are anesthetized with sodium pentobarbital (30 mg/kg, i.v.). After deep anesthesia is achieved (determined by the absence of an ocular blink reflex) the animal is intubated and ventilated with 100% O$_2$ using a positive pressure ventilator. A left thoracotomy is performed, the heart exposed, and a snare (2-0 silk) is placed loosely around a branch of the left anterior descending coronary artery, approximately ⅔ of the distance towards the apex of the heart. The heart is removed from the chest and rapidly (<30 cc) mounted on a Langendorff apparatus. The heart is retrogradely used via the aorta in a non-recirculating manner with a modified Krebs solution (NaCl 118.5 mM, KCl 4.7 mM, Mg SO$_4$ 1.2 mM, KH$_2$PO$_4$ 1.2 mM, NaHCO$_3$ 24.8 mM, CaCl$_2$ 2.5 mM, and glucose 10 mM), at a constant pressure of 80 mmHg and a temperature of 37° C. Perfusate pH is maintained at 7.4–7.5 by bubbling with 95% O$_2$/5% CO$_2$. Heart temperature is tightly controlled by using heated reservoirs for the physiological solution and water jacketing around both the perfusion tubing and the isolated heart. Heart rate and left ventricular pressures are determined via a latex balloon which is inserted in the left ventricle and connected by stainless steel tubing to a pressure transducer. The intraventricular balloon is inflated to provide a systolic pressure of 80–100 mmHg, and a diastolic pressure less than or equal to 10 mmHg. Perfusate flow rates are routinely determined throughout the experimental period.

The heart is allowed to equilibrate for 30 min, over which time the heart must show stable left ventricular pressures within the parameters outlined above. If the heart rate falls below 180 bpm at any time prior to the 30 min period of regional ischemia, the heart is paced at ≈200 bpm for the remainder of the experiment. ischemic preconditioning is induced by total cessation of cardiac perfusion (global ischemia) for 5 min, followed by reperfusion for 10 min. The global ischemia/reperfusion is repeated one additional time, followed by a 30 min regional ischemia. The regional ischemia is provided by tightening the snare around the coronary artery branch. Following the 30 min regional ischemia, the snare is released and the heart reperfused for an additional 120 min.

Pharmacological cardioprotection is induced by infusing the test compound at predetermined concentrations, starting 30 min prior to the 30 min regional ischemia, and continuing until the end of the 120 min reperfusion period. Hearts which receive test compounds do not undergo the two periods of ischemic preconditioning. The reference compound, APNEA (500 nM) is perfused through hearts (which do not receive the test compound) for a 5 min period which ends 10 min before the 30 min regional ischemia.

At the end of the 120 min reperfusion period, the coronary artery snare is tightened, and a 0.5% suspension of fluorescent zinc cadmium sulfate particles (1–10 $\mu$M) is perfused through the heart; this stains all of the myocardium, except that area at risk for infarct development (area-at-risk). The heart is removed from the Langendorff apparatus, blotted dry, weighed, wrapped in aluminum foil and stored overnight at $-20°$ C. The next day, the heart is sliced into 2 mm transverse sections from the apex to just above the coronary artery snare. The slices are stained with 1% triphenyl tetrazolium chloride (TTC) in phosphate-buffered saline for 20 min at $37°$ C. Since TTC reacts with living tissue (containing NAD-dependent dehydrogenases), this stain differentiates between living (red stained) tissue, and dead tissue (unstained infarcted tissue). The infarcted area (no stain) and the area-at-risk (no fluorescent particles) are calculated for each slice of left ventricle using a precalibrated image analyzer. To normalize the ischemic injury for difference in the area-at-risk between hearts, the data is expressed as the ratio of infarct area vs. area-at-risk (%IA/AR).

The activity and thus utility of the compounds of the present invention as medical agents in providing protection from ischemic damage to tissue in a mammal can be further demonstrated by the activity of the compounds in the in vitro assay described below. The assay also provides a means whereby the activities of the compounds of the present invention can be compared with the activities of other known compounds. The results of these comparisons are useful for determining dosage levels in mammals, including humans, for inducing protection from ischemia.

The activity of a sorbitol dehydrogenase inhibitor in a tissue can be determined by testing the amount of sorbitol dehydrogenase inhibitor that is required to raise tissue sorbitol (i.e., by inhibiting the further metabolism of sorbitol consequent to blocking sorbitol dehydrogenase) or lower tissue fructose (by inhibiting its production from sorbitol consequent to blocking sorbitol dehydrogenase). While not wishing to be bound by any particular theory or mechanism, it is believed that a sorbitol dehydrogenase inhibitor, by inhibiting sorbitol dehydrogenase, prevents or reduces ischemic damage as described hereinafter in the following paragraph and scheme, appearing at column 9 of U.S. Pat. No. 5,932,581, which is hereby incorporated by reference herein.

When the supply of oxygenated blood to a tissue is interrupted or slowed down (ischemia) the cells in the oxygen-deficient tissue derive their energy (ATP) from glucose via glycolysis (which does not require the presence of oxygen). Glycolysis also requires a supply of NAD$^+$ and in an ischemic tissue the length of time glycolysis can be maintained becomes sensitive to the supply of NAD$^+$. However, sorbitol dehydrogenase (SDH) also utilizes NAD$^+$ but does not produce an increase in ATP. Thus, it follows that preventing or retarding NAD$^+$ use by SDH with sorbitol dehydrogenase inhibitors (SDIs) will enhance or prolong the ability of ischemic tissue to carry out glycolysis, i.e., to produce energy in the absence of oxygen and in turn enhance and prolong the survival of the cells in the tissue. Since inhibition of SDH will retard depletion of the tissue's NAD$^+$, a sorbitol dehydrogenase inhibitor is an effective anti-ischemic agent.

Again, the activity of a sorbitol dehydrogenase inhibitor can be determined by the amount of sorbitol dehydrogenase inhibitor that is required to raise tissue sorbitol or lower tissue fructose. Male Sprague-Dawley rats are rendered diabetic by injection of streptozocin at 55 mg/kg, i.v., in pH 4.5 citrate buffer. They are fed ad libitum in controlled conditions of housing, temperature and lighting. After five weeks of diabetes, the rats are anesthetized with an overdose of pentobarbital, and tissues are rapidly removed and analyzed for sorbitol and fructose. Sorbitol levels are analyzed according to the method of Donald M. Eades et al., "Rapid Analysis of Sorbitol, Galactitol, Mannitol and Myoinositol Mixtures From Biological Sources," *Journal of Chromatography*, 490, 1–8, (1989).

Fructose in rat tissues is enzymatically measured using a modification of the method of Ameyama (*Methods in Enzymology*, 89:20–29 1982), in which ferricyamide was replaced by resazurin, a dye that is reduced to the highly fluorescent resorufin. The amount of resorufin fluorescence is stoichiometric with the amount of fructose oxidized by fructose dehydrogenase. The assay contains 0.1 ml neutralized 6% perchloric acid nerve extract in a final volume of 1.5 ml. Following incubation for 60 minutes at room temperature in a closed drawer, sample fluorescence is determined at excitation=560 nm, emission=580 nm with slits of 5 mm each on a Perkin-Elmer model 650–40 fluorescence spectrophotometer. Fructose concentrations are calculated by comparison with a series of known fructose standards.

The sorbitol dehydrogenase inhibitor compounds of the present invention are thus useful in reducing or minimizing damage effected directly to any tissue that may be susceptible to ischemia/reperfusion injury (e.g., heart, brain, lung, kidney, liver, gut, skeletal muscle, retina) as the result of an ischemic event (e.g., myocardial infarction). A compound of the present invention is therefore usefully employed prophylactically to prevent, i.e. (prospectively or prophylactically) to blunt or stem, tissue damage (e.g., myocardial tissue) in patients who are at risk for ischemia (e.g., myocardial ischemia).

The sorbitol dehydrogenase inhibitor compounds of the present invention are particularly well suited to the treatment of diabetic patients because of increased metabolism through sorbitol dehydrogenase in the diabetic state. The compounds of the present invention are also well suited for prophylactic use with non-diabetic patients who have actually suffered or who are considered at risk of suffering from ischemic events (e.g., myocardial ischemia).

The compounds of formula I of the present invention may be administered to a subject in need of treatment by a variety of conventional routes of administration, including orally, parenterally, topically and rectally, as described further below. In general, compounds of formula I and their pharmaceutically acceptable salts will be administered orally or parenterally at dosages between about 0.001 and about 100 mg/kg body weight of the subject to be treated per day, preferably from about 0.01 to 10 mg/kg, in single or divided doses. However, some variation in dosage will necessarily occur depending on the condition of the subject being treated. The individual responsible for dosing will, in any event, determine the appropriate dose for the individual subject.

Mutual prodrugs of compounds of formula I and aldose reductase inhibitors, as described below, will generally be administered orally or parenterally at dosages between about 0.001 and about 100 mg/kg body weight of the subject to be treated per day, preferably from about 0.01 to about 10 mg/kg, in single or divided doses. Compositions containing both a compound of the formula I and an aldose reductase inhibitor will generally be administered orally or parenterally at dosages between about 0.001 and about 100 mg of each active component (i.e., the compound of formula I and the aldose reductase inhibitor) per kg body weight of the subject to be treated per day, preferably from about 0.01 to about 10 mg/kg.

The following compounds of the present invention are preferred:

4-(4-hydroxymethyl-[1,3,5]triazin-2-yl)-piperazine-1-sulfonic acid dimethylamide;

1-{4-[3R, 5S-dimethyl-4-(4-methyl-[1,3,5]triazin-2-yl)-piperazin-1-yl]-[1,3,5]triazin-2-yl}-R-ethanol;

1-{4-[4-(4-hydroxymethyl-[1,3,5]triazin-2-yl)-3R,5S-dimethyl-piperazin-1-yl]-[1,3,5]triazin-2-yl}-ethanol;

2-{4-[4-(4-hydroxymethyl-[1,3,5]triazin-2-yl)-3R,5S-dimethyl-piperazin-1-yl]-6-methyl-[1,3,5]triazin-2-yl}-phenol;

1-{4-[4-(4-cyclopropyl-[1,3,5]triazin-2-yl)-3R,5S-dimethyl-piperazin-1-yl]-[1,3,5]triazin-2-yl}-ethanol;

dimethylamino-acetic acid 1-{4-[3R,5S-dimethyl-4-(4-methyl-[1,3,5]triazin-2-yl)-piperazin-1-yl]-[1,3,5]triazin-2-yl}-ethyl ester;

4-[4-(1-hydroxy-ethyl)-[1,3,5]triazin-2-yl]-piperazine-1-sulfonic acid dimethylamide;

1-(4-{4-[4-(1-hydroxy-ethyl)-[1,3,5]triazin-2-yl]-2R,6S-dimethyl-piperazin-1-yl}-[1,3,5]triazin-2-yl)-ethanol;

1-{4-[4-(4-phenyl-[1,3,5]triazin-2-yl)-2R,6S-dimethyl-piperazin-1-yl]-[1,3,5]triazin-2-yl}-methanol;

1-{4-[4-(4-hydroxy-3-methyl-[1,3,5]triazin-2-yl)-3R,5S-dimethyl-piperazin-1-yl]-[1,3,5]triazin-2-yl}-ethanol;

1-{4-[4-(4-phenyl-[1,3,5]triazin-2-yl)-3R,5S-dimethyl-piperazin-1-yl]-[1,3,5]triazin-2-yl}-methanol;

1-{4-[4-(4-methoxymethy-[1,3,5]triazin-2-yl)-2R,6S-dimethyl-piperazin-1-yl]-[1,3,5]triazin-2-yl}-methanol;

1-{4-[4-(4-hydroxymethyl-[1,3,5]triazin-2-yl)-3R,5S-dimethyl-piperazin-1-yl]-[1,3,5]triazin-2-yl}-methanol;

1-{4-[4-(4-methoxy-6-methyl-[1,3,5]triazin-2-yl)-3R,5S-dimethyl-piperazin-1-yl]-[1,3,5]triazin-2-yl}-methanol;

1-{4-[4-(4-phenyl -[1,3,5]triazin-2-yl)-3R,5S-dimethyl-piperazin-1-yl]-[1,3,5]triazin-2-yl}-ethanol;

1-{4-[4-(4-hydroxy-6-phenyl-[1,3,5]triazin-2-yl)-3R,5S-dimethyl-piperazin-1-yl]-[1,3,5]triazin-2-yl}-ethanol;

benzofuran-2-yl-{4-[4-1-hydroxy-ethyl)-[1,3,5]triazin-2-yl]-2R,6S-dimethyl-piperazin-1-yl}-methanone; and furo[2,3-c]pyridin-2-yl-{4-[4-1-hydroxy-ethyl)-[1,3,5]triazin-2-yl]-2R,6S-dimethyl-piperazin-1-yl}-methanone.

The term "Second Agents" hereinafter refers collectively to pharmaceutical compounds or agents that are aldose reductase inhibitors, sodium hydrogen ion exchange (NHE-1) inhibitors, glycogen phosphorylase inhibitors, selective serotonin reuptake inhibitors, 3-hydroxy-3-methylglutaryl coenzyme A reductase inhibitors, angiotensin converting enzyme inhibitors, thiazolidinedione antidiabetic agents, angiotensin II receptor antagonists, γ-aminobutyric acid (GABA) agonist, phosphodiesterase type 5 inhibitors or CETP inhibitors, a prodrug of said compounds or agents, or a pharmaceutically acceptable salt of such compounds, agents or prodrugs. Use of the term in singular form, as in "a Second Agent" hereinafter refers to a pharmaceutical agent selected from said Second Agents. A Second Agent may be a pharmaceutical agent that shares more than one of the foregoing characteristics.

An additional aspect of this invention relates to pharmaceutical compositions comprising a compound of formula I of the present invention, and a Second Agent. Such compositions are hereinafter referred to collectively as the "combination compositions".

This invention also relates to therapeutic methods for treating or preventing diabetic complications in a mammal wherein a compound of formula I of the present invention and a Second Agent are administered together as part of the same pharmaceutical composition or separately. Such methods are hereinafter referred to collectively as the "combination therapies" of the present invention. Combination therapies include therapeutic methods wherein a compound of formula I of the present invention and a Second Agent are administered together as part of the same pharmaceutical composition and to methods wherein these two agents are administered separately, either simultaneously or sequentially in any order.

This invention further provides pharmaceutical kits comprising a compound of formula I of the present invention and a Second Agent. Such kits may hereinafter be referred to as the "kits" of the present invention.

Any aldose reductase inhibitor may be used as the Second Agent in the combination compositions, combination therapies and kits of the present invention. The term aldose reductase inhibitor refers to compounds which inhibit the bioconversion of glucose to sorbitol catalyzed by the enzyme aldose reductase. Such inhibition is readily determined by those skilled in the art according to standard assays (J. Malone, Diabetes, 29:861–864, 1980. "Red Cell Sorbitol, an Indicator of Diabetic Control"). A variety of aldose reductase inhibitors are described and referenced below; however, other aldose reductase inhibitors will be known to those skilled in the art. The disclosures of U.S. patents listed below are hereby incorporated by reference. Also, common chemical USAN names or other designation are in parentheses where applicable, together with reference to appropriate patent literature disclosing the compound.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose).

Accordingly, examples of aldose reductase inhibitors useful in the compositions and methods of this invention include:

1. 3-(4-bromo-2-fluorobenzyl)-3,4-dihydro-4-oxo-1-phthalazineacetic acid (ponalrestat, U.S. Pat. No. 4,251,528);

2. N[[(5-trifluoromethyl)-6-methoxy-1-naphthalenyl]thioxomethyl]-N-methylglycine (tolrestat, U.S. Pat. No. 4,600,724);

3. 5-[(Z,E)-β-methylcinnamylidene]-4-oxo-2-thioxo-3-thiazolideneacetic acid (epalrestat, U.S. Pat. Nos. 4,464,382, 4,791,126, 4,831,045);

4. 3-(4-bromo-2-fluorobenzyl)-7-chloro-3,4-dihydro-2,4-dioxo-1 (2H)-quinazolineacetic acid (zenarestat, U.S. Pat. Nos. 4,734,419, and 4,883,800);

5. 2R,4R-6,7-dichloro-4-hydroxy-2-methylchroman-4-acetic acid (U.S. Pat. No. 4,883,410);

6. 2R,4R-6,7-dichloro-6-fluoro-4-hydroxy-2-methylchroman-4-acetic acid (U.S. Pat. No. 4,883,410);

7. 3,4-dihydro-2,8-diisopropyl-3-oxo-2H-1,4-benzoxazine-4-acetic acid (U.S. Pat. No. 4,771,050);

8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);

9. N-[3,5-dimethyl-4-[(nitromethyl)sulfonyl]phenyl]-2-methyl-benzeneacetamide (ZD5522, U.S. Pat. Nos. 5,270,342 and 5,430,060);

10. (S)-6-fluorospiro[chroman-4,4'-imidazolidine]-2,5'-dione (sorbinil, U.S. Pat. No. 4,130,714);

11. d-2-methyl-6-fluoro-spiro(chroman-4',4'-imidazolidine)-2',5'-dione (U.S. Pat. No. 4,540,704);

12. 2-fluoro-spiro(9H-fluorene-9,4'-imidazolidine)-2',5'-dione (U.S. Pat. No. 4,438,272);

13. 2,7-di-fluoro-spiro(9H-fluorene-9,4'-imidazolidine)-2',5'-dione (U.S. Pat. Nos. 4,436,745, 4,438,272);

14. 2,7-di-fluoro-5-methoxy-spiro(9H-fluorene-9,4'-imidazolidine)-2',5'-dione (U.S. Pat. Nos. 4,436,745, 4,438,272);

15. 7-fluoro-spiro(5H-indenol[1,2-b]pyridine-5,3'-pyrrolidine)-2,5'-dione (U.S. Pat. Nos. 4,436,745, 4,438,272);

16. d-cis-6'-chloro-2',3'-dihydro-2'-methyl-spiro-(imidazolidine-4,4'-4'H-pyrano(2,3-b) pyridine)-2,5-dione (U.S. Pat. No. 4,980,357);

17. spiro[imidazolidine-4,5'(6H)-quinoline]-2,5-dione-3'-chloro-7',8'-dihydro-7'-methyl-(5'-cis) (U.S. Pat. No. 5,066,659);

18. (2S,4S)-6-fluoro-2',5'-dioxospiro(chroman-4,4'-imidazolidine)-2-carboxamide (U.S. Pat. No. 5,447,946); and 19. 2-[(4-bromo-2-fluorophenyl)methyl]-6-fluorospiro[isoquinoline-4(1H), 3'-pyrrolidine]-1,2',3,5'(2H)-tetrone (ARI-509, U.S. Pat. No. 5,037,831).

Other aldose reductase inhibitors include compounds such as those disclosed in U.S. Pat. No. 4,939,140, and having the formula ARI,

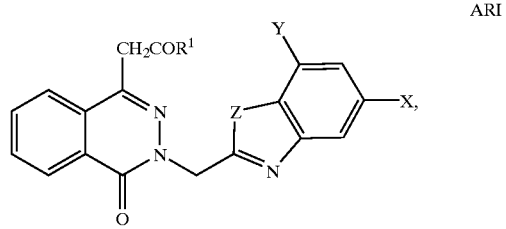

ARI or a pharmaceutically acceptable salt thereof, wherein

Z in the compounds of formula ARI is O or S;

$R^1$ in the compounds of formula ARI is hydroxy or a group capable of being removed in vivo to produce a compound of formula ARI wherein $R^1$ is OH; and X and Y in the compounds of formula ARI are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of Formula ARI:

20. 3,4-dihydro-3-(5-fluorobenzothiazol-2-ylmethyl)-4-oxophthalazin-1-yl-acetic acid [$R^1$=hydroxy; X=F; Y=H];

21. 3-(5,7-difluorobenzothiazol-2-ylmethyl)-3,4-dihydro-4-oxophthalazin-1-ylacetic acid [$R^1$=hydroxy; X=Y=F];

22. 3-(5-chlorobenzothiazol-2-ylmethyl)-3,4-dihydro-4-oxophthalazin-1-ylacetic acid [$R^1$=hydroxy; X=Cl; Y=H];

23. 3-(5,7-dichlorobenzothiazol-2-ylmethyl)-3,4-dihydro-4-oxophthalazin-1-ylacetic acid [$R^1$=hydroxy; X=Y=Cl];

24. 3,4-dihydro-4-oxo-3-(5-trifluoromethylbenzoxazol-2-ylmethyl)phthalazin-1-ylacetic acid [$R^1$=hydroxy; X=CF_3$; Y=H];

25. 3,4-dihydro-3-(5-fluorobenzoxazol-2-ylmethyl)-4-oxophthalazin-1-yl-acetic acid [$R^1$=hydroxy; X=F; Y=H];

26. 3-(5,7-difluorobenzoxazol-2-ylmethyl)-3,4-dihydro-4-oxophthalazin-1-ylacetic acid [$R^1$=hydroxy; X=Y=F];

27. 3-(5-chlorobenzoxazol-2-ylmethyl)-3,4-dihydro-4-oxophthalazin-1-ylacetic acid [$R^1$=hydroxy; X=Cl; Y=H];

28. 3-(5,7-dichlorobenzoxazol-2-ylmethyl)-3,4-dihydro-4-oxophthalazin-1-ylacetic acid [$R^1$=hydroxy; X=Y=Cl]; and 29. zopolrestat; 1-phthalazineacetic acid, 3,4-dihydro-4-oxo-3-[[5-(trifluoromethyl)-2-benzothiazolyl]methyl]-[$R^1$=hydroxy; X=trifluoromethyl; Y=H].

In compounds 20–23, and 29, Z is S. In compounds 24–28, Z is O.

Of the above subgroup, compounds 20–29 are more preferred with 29 especially preferred.

An especially preferred aldose reductase inhibitor is 1-phthalazineacetic acid, 3,4-dihydro-4-oxo-3-[[5-trifluoromethyl)-2-benzothiazolyl]methyl]-.

The term "acyl radical of a carboxylic acid aldose reductase inhibitor" refers to any of the above-mentioned aldose reductase inhibitors which contains a carboxylic acid group in which the carboxylic acid group is replaced with a carbonyl radical.

The aldose reductase inhibitor compounds of this invention are readily available or can be easily synthesized by those skilled in the art using conventional methods of organic synthesis, particularly in view of the pertinent patent specification descriptions.

An amount of the aldose reductase inhibitor of this invention that is effective for the uses of the present invention may be used. Typically, an effective dosage for the aldose reductase inhibitors of this invention is in the range of about 0.1 mg/kg/day to 100 mg/kg/day in single or divided doses, preferably 0.1 mg/kg/day to 20 mg/kg/day in single or divided doses.

Any sodium hydrogen ion exchange (NHE-1) inhibitor may be used as the Second Agent in the combination compositions, combination therapies and kits of the present invention. The term NHE-1 inhibitor refers to compounds which inhibit the sodium/proton ($Na^+/H^+$) exchange transport system and hence are useful as a therapeutic or prophylactic agent for diseases caused or aggravated by the acceleration of the sodium/proton ($Na^+/H^+$) exchange transport system, for example, cardiovascular diseases (e.g., arteriosclerosis, hypertension, arrhythmia (e.g. ischemic arrhythmia, arrhythmia due to myocardial infarction, myocardial stunning, myocardial dysfunction, arrhythmia after percutaneous transluminal coronary angioplasty (PTCA) or after thrombolysis, etc.), angina pectoris, cardiac hypertrophy, myocardial infarction, heart failure (e.g., congestive heart failure, acute heart failure, cardiac hypertrophy, etc.), restenosis after PTCA, PTCI, shock (e.g., hemorrhagic shock, endotoxin shock, etc.)), renal diseases (e.g., diabetes mellitus, diabetic nephropathy, ischemic acute renal failure, etc.) organ disorders associated with ischemia or ischemic reperfusion (e.g., heart muscle ischemic reperfusion associated disorders, acute renal failure, or disorders induced by surgical treatment such as coronary artery bypass grafting (CABG) surgeries, vascular surgeries, organ transplantation, non-cardiac surgeries or percutaneous transluminal coronary angioplasty (PTCA)), cerebrovascular diseases (e.g., ischemic stroke, hemorrhagic stroke, etc.), cerebro ischemic disorders (e.g., disorders associated with cerebral infarction, disorders caused after cerebral apoplexy as sequelae, or cerebral edema).

NHE-1 inhibitors are disclosed in U.S. Pat. No. 5,698, 581; European Patent Application Publication No. EP 803 501 A1; and International Patent Application Publication Nos. WO 94/26709; and WO 98/26803; each of which is incorporated herein by reference. The NHE-1 inhibitors disclosed therein have utility in the combination aspects of the present invention. Said NHE-1 inhibitors can be prepared as disclosed therein.

Preferred NHE-1 inhibitors include compounds of the formula NHE,

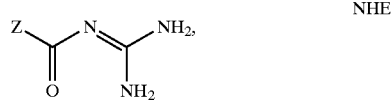

NHE prodrugs thereof or pharmaceutically acceptable salts of said compounds and said prodrugs, wherein the variables are as defined in International Patent Application Publication No. WO 99/43663, which is incorporated herein by reference.

Especially preferred NHE-1 inhibitors include [1-(8-bromoquinolin-5-yl)-5-cyclopropyl-1H-pyrazole-4-carbonyl]guanidine; [1-(6-chloroquinolin-5-yl)-5-cyclopropyl-1H-pyrazole-4-carbonyl]guanidine; [1-(indazol-7-yl)-5-cyclopropyl-1H-pyrazole-4-carbonyl]guanidine; [1-(benzimidazol-5-yl)-5-cyclopropyl-1H-pyrazole-4-carbonyl]guanidine; [1-(1-isoquinolyl)-5-cyclopropyl-1H-pyrazole-4-carbonyl]guanidine; [5-cyclopropyl-1-(4-quinolinyl)-1H-pyrazole-4-carbonyl] guanidine; [5-cyclopropyl-1-(quinolin-5-yl)-1H-pyrazole-4-carbonyl]guanidine; [5-cyclopropyl-1-(quinolin-8-yl)-1H-pyrazole-4-carbonyl]guanidine; [1-(indazol-6-yl)-5-ethyl-1H-pyrazole-4-carbonyl]guanidine; [1-(indazol-5-yl)-5-ethyl-1H-pyrazole-4-carbonyl]guanidine; [1-(benzimidazol-5-yl)-5-ethyl-1H-pyrazole-4-carbonyl]guanidine; [1-(1-methylbenzimidazol-6-yl)-5-ethyl-1H-pyrazole-4-carbonyl] guanidine; [1-(5-quinolinyl)-5-n-propyl-1H-pyrazole-4-carbonyl]guanidine; [1-(5-quinolinyl)-5-isopropyl-1H-pyrazole-4-carbonyl]guanidine; [5-ethyl-1-(6-quinolinyl)-1H-pyrazole-4-carbonyl]guanidine; [1-(2-methylbenzimidazol-5-yl)-5-ethyl-1H-pyrazole-4-carbonyl] guanidine; [1-(1,4-benzodioxan-6-yl)-5-ethyl-1H-pyrazole-4-carbonyl]guanidine; [1-(benzotriazol-5-yl)-5-ethyl-1H-pyrazole-4-carbonyl]guanidine; [1-(3-chloroindazol-5-yl)-5-ethyl-1H-pyrazole-4-carbonyl]guanidine; [1-(5-quinolinyl)-5-butyl-1H-pyrazole-4-carbonyl]guanidine; [5-propyl-1-(6-quinolinyl)-1H-pyrazole-4-carbonyl] guanidine; [5-isopropyl-1-(6-quinolinyl)-1H-pyrazole-4-carbonyl]guanidine; [1-(2-chloro-4-methylsulfonylphenyl)-5-cyclopropyl-1H-pyrazole-4-carbonyl]guanidine; [1-(2-chlorophenyl)-5-cyclopropyl-1H-pyrazole-4-carbonyl] guanidine; [1-(2-trifluoromethyl-4-fluorophenyl)-5-cyclopropyl-1H-pyrazole-4-carbonyl]guanidine; [1-(2-bromophenyl)-5-cyclopropyl-1H-pyrazole-4-carbonyl] guanidine; [1-(2-fluorophenyl)-5-cyclopropyl-1H-pyrazole-4-carbonyl]guanidine; [1-(2-chloro-5-methoxyphenyl)-5-cyclopropyl-1H-pyrazole-4-carbonyl]guanidine; [1-(2-chloro-4-methylaminosulfonylphenyl)-5-cyclopropyl-1H-pyrazole-4-carbonyl]guanidine; [1-(2,5-dichlorophenyl)-5-cyclopropyl-1H-pyrazole-4-carbonyl]guanidine; [1-(2,3-dichlorophenyl)-5-cyclopropyl-1H-pyrazole-4-carbonyl] guanidine; [1-(2-chloro-5-aminocarbonylphenyl)-5-cyclopropyl-1H-pyrazole-4-carbonyl]guanidine; [1-(2-chloro-5-aminosulfonylphenyl)-5-cyclopropyl-1H-pyrazole-4-carbonyl]guanidine; [1-(2-fluoro-6-trifluoromethylphenyl)-5-cyclopropyl-1H-pyrazole-4-carbonyl]guanidine; [1-(2-chloro-5-methylsulfonylphenyl)-5-cyclopropyl-1H-pyrazole-4-carbonyl]guanidine; [1-(2-chloro-5-dimethylaminosulfonylphenyl)-5-cyclopropyl-1H-pyrazole-4-carbonyl]guanidine; [1-(2-trifluoromethyl-4-chlorophenyl)-5-cyclopropyl-1H-pyrazole-4-carbonyl] guanidine; [1-(2-chlorophenyl)-5-methyl-1H-pyrazole-4-carbonyl]guanidine; [5-methyl-1-(2-trifluoromethylphenyl)-1H-pyrazole-4-carbonyl]guanidine; [5-ethyl-1-phenyl-1H-pyrazole-4-carbonyl]guanidine; [5-cyclopropyl-1-(2-trifluoromethylphenyl)-1H-pyrazole-4-carbonyl] guanidine; [5-cyclopropyl-1-phenyl-1H-pyrazole-4-carbonyl]guanidine; [5-cyclopropyl-1-(2,6-dichlorophenyl)-1H-pyrazole-4-carbonyl]guanidine; and pharmaceutically acceptable salts thereof.

The preferred and especially preferred NHE-1 inhibitors disclosed in the above two paragraphs can be prepared according to methods set forth in International Patent Application Publication No. WO 99/43663, as referenced above.

Preferably, the compounds of formula I of this invention can be used in combination with NHE-1 inhibitors as agents for myocardial protection before, during, or after coronary artery bypass grafting (CABG) surgeries, vascular surgeries, percutaneous transluminal coronary angioplasty (PTCA), organ transplantation or non-cardiac surgeries. Preferably, the compounds of formula I of this invention can be used in combination with NHE-1 inhibitors as agents for myocardial protection in patients presenting with ongoing cardiac (acute coronary syndromes, e.g., myocardial infarction or unstable angina) or cerebral ischemic events (e.g., stroke). Preferably, the compounds of formula I of this invention can be used in combination with NHE-1 inhibitors as agents for chronic myocardial protection in patients with diagnosed coronary heart disease (e.g., previous myocardial infarction or unstable angina) or patients who are at high risk for myocardial infarction (age greater than 65 and two or more risk factors for coronary heart disease).

In addition, a combination of the compounds of formula I of the present invention and NHE-1 inhibitors has a strong inhibitory effect on the proliferation of cells, for example the proliferation of fibroblast cells and the proliferation of the smooth muscle cells of the blood vessels. For this reason, the combination of the compounds of formula I of the present invention and NHE-1 inhibitors is a valuable therapeutic agent for use in diseases in which cell proliferation represents a primary or secondary cause and may, therefore, be used as antiatherosclerotic agents, and as agents against diabetic late complications, cancerous diseases, fibrotic diseases such as pulmonary fibrosis, hepatic fibrosis or renal fibrosis, glomerular nephrosclerosis, organ hypertrophies or hyperplasias, in particular hyperplasia or hypertrophy of the prostate, pulmonary fibrosis, diabetic complications or recurrent stricture after PTCA, or diseases caused by endothelial cell injury.

The utility of the combination of compounds of the present invention and NHE-1 inhibitors as medical agents in the treatment of diseases, such as are detailed herein, in mammals (e.g., humans), for example, myocardial protection during surgery or myocardial protection in patients presenting with ongoing cardiac or cerebral ischemic events or chronic cardioprotection in patients with diagnosed coronary heart disease, or at risk for coronary heart disease, cardiac dysfunction or myocardial stunning is demonstrated by the activity of said combination in conventional preclinical cardioprotection assays, as reported in the scientific literature and in WO 99/43663. The therapeutic effects of the combination of the compounds of formula I of the present invention and NHE-1 inhibitors in preventing heart tissue damage resulting from an ischemic insult can be demonstrated in vitro utilizing procedures reported in the scientific literature and in WO 99/43663. The therapeutic effects of a combination of a compound of formula I of the present invention and an NHE-1 inhibitor in preventing heart tissue damage otherwise resulting from an ischemic insult can also be demonstrated in vivo utilizing procedures reported in the scientific literature and in WO 99/43663.

The combination of a compound of formula I of the present invention and an NHE-1 inhibitor can be tested for their utility in reducing or preventing ischemic injury in non-cardiac tissues, for example, the brain, or the liver, utilizing procedures reported in the scientific literature and in WO 99/43663. The combination of a compound of formula I of the present invention and an NHE-1 inhibitor in such tests can be administered by the preferred route and vehicle of administration and at the preferred time of administration either prior to the ischemic episode, during the ischemic episode, following the ischemic episode (reperfusion period) or during any of the experimental stages, as referenced herein.

Compositions containing both a compound of formula I of the present invention and a NHE-1 inhibitor will generally be administered orally or parenterally at dosages between about 0.001 and 100 mg of said compound of formula I of the present invention per kg body weight of the subject to be treated per day and about 0.001 to 100 mg/kg/day of the NHE-1 inhibitor. An especially preferred dosage contains between about 0.01 and 10 mg/kg/day of said compound of formula I of the present invention and between about 0.01 and 50 mg/kg/day of said NHE-1 inhibitor. The compositions of the present invention comprising a compound of formula I of the present invention in combination with an NHE-1 inhibitor are useful, for example, in reducing or minimizing damage effected directly to any tissue that may be susceptible to ischemia/reperfusion injury (e.g., heart, brain, lung, kidney, liver, gut, skeletal muscle, retina) as the result of an ischemic event (e.g., myocardial infarction). Therefore, the composition is usefully employed prophylactically to prevent, i.e. (prospectively or prophylactically) to blunt or stem tissue damage (e.g., myocardial tissue) in patients who are at risk for ischemia (e.g., myocardial ischemia).

Any glycogen phosphorylase inhibitor may be used as the Second Agent in the combination compositions, combination therapies and kits of the present invention. The term glycogen phosphorylase inhibitor refers to any substance or agent or any combination of substances and/or agents which reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays known in the art. A variety of these compounds are included in U.S. Pat. No. 5,988,463 and in the following published PCT patent applications: WO 96/39384 and WO96/39385. However, other glycogen phosphorylase inhibitors will be known to those skilled in the art.

Compositions containing both a compound of formula I and a glycogen phosphorylase inhibitor will generally be administered orally or parenterally at dosages between about 0.001 and 100 mg of said compound of formula I of the present invention per kg body weight of the subject to be treated per day and 0.005 to 50 mg/kg/day of said glycogen phosphorylase inhibitor, preferably 0.01 and 10 mg/kg/day of said compound of formula I of the present invention and 0.01 to 25 mg/kg/day of said glycogen phosphorylase inhibitor, and most preferably 0.01 and 10 mg/kg/day of said compound of formula I of the present invention and 0.1 to 15 mg/kg/day of said glycogen phosphorylase inhibitor. However, some variation in dosage will necessarily occur depending on the condition of the subject being treated. The person responsible for administration will, in any event, determine the appropriate dose for the individual subject.

Any selective serotonin reuptake inhibitor (SSRI) may be used as the Second Agent in the combination compositions, combination therapies and kits of the present invention. The term selective serotonin reuptake inhibitor refers to an agent which inhibits the reuptake of serotonin by afferent neurons. Such inhibition is readily determined by those skilled in the art according to standard assays such as those disclosed in U.S. Pat. No. 4,536,518 and other U.S. patents recited in the next paragraph.

Preferred selective serotonin reuptake inhibitors which may be used in accordance with the present invention include femoxetine, which may be prepared as described in U.S. Pat. No. 3,912,743; fluoxetine, which may be prepared as described in U.S. Pat. No. 4,314,081; fluvoxamine, which may be prepared as described in U.S. Pat. No. 4,085,225; indalpine, which may be prepared as described in U.S. Pat. No. 4,064,255; indeloxazine, which may be prepared as described in U.S. Pat. No. 4,109,088; milnacipran, which may be prepared as described in U.S. Pat. No. 4,478,836; paroxetine, which may be prepared as described in U.S. Pat. No. 3,912,743 or U.S. Pat. No. 4,007,196; sertraline and its pharmaceutically acceptable acid addition salts, such as the hydrochloride salt, which may be prepared as described in U.S. Pat. No. 4,536,518; sibutramine, which may be prepared as described in U.S. Pat. No. 4,929,629; and zimeldine, which may be prepared as described in U.S. Pat. No. 3,928,369. Fluoxetine is also known as Prozac®. Sertraline hydrochloride is also known as Zoloft®. Sibutramine is also known as Meridia®. The disclosures thereof are incorporated herein by reference.

Selective serotonin reuptake inhibitors are preferably administered in amounts ranging from about 0.01 mg/kg/day to about 500 mg/kg/day in single or divided doses, preferably about 10 mg to about 300 mg per day for an average subject, depending upon the selective serotonin reuptake inhibitor and the route of administration. However, some variation in dosage will necessarily occur depending on the condition of the subject being treated. The individual responsible for dosing will, in any event, determine the appropriate dose for the individual subject.

Any 3-hydroxy-3-methylglutaryl coenzyme A (HMG-CoA) reductase inhibitor may be used as the Second Agent in the combination compositions, combination therapies and kits of the present invention. The term 3-hydroxy-3-methylglutaryl coenzyme A (HMG-CoA) reductase inhibitor refers to a pharmaceutical agent which inhibits the enzyme 3-hydroxy-3-methylglutaryl-coenzyme A (HMG-CoA) reductase. This enzyme is involved in the conversion of HMG-CoA to mevalonate, which is one of the steps in cholesterol biosynthesis. Such inhibition is readily determined according to standard assays well known to those skilled in the art.

Preferred 3-hydroxy-3-methylglutaryl coenzyme A reductase inhibitors which may be used in accordance with the present invention include atorvastatin, disclosed in U.S. Pat. No. 4,681,893, atorvastatin calcium, disclosed in U.S. Pat. No. 5,273,995, cerivastatin, disclosed in U.S. Pat. No. 5,502,199, dalvastatin, disclosed in European Patent Application Publication No. 738,510 A2, fluindostatin, disclosed in European Patent Application Publication No. 363,934 A1, fluvastatin, disclosed in U.S. Pat. No. 4,739,073, lovastatin, disclosed in U.S. Pat. No. 4,231,938, mevastatin, disclosed in U.S. Pat. No. 3,983,140, pravastatin, disclosed in U.S. Pat. No. 4,346,227, simvastatin, disclosed in U.S. Pat. No. 4,444,784 and velostatin, disclosed in U.S. Pat. No. 4,448,784 and U.S. Pat. No. 4,450,171, all of which are incorporated herein by reference. Especially preferred 3-hydroxy-3-methylglutaryl coenzyme A reductase inhibitors include atorvastatin, atorvastatin calcium, also known as Lipitor®, lovastatin, also known as Mevacor®, pravastatin, also known as Pravachol®, and simvastatin, also known as Zocor®.

3-Hydroxy-3-methylglutaryl coenzyme A reductase inhibitors are preferably administered in amounts ranging from about 0.1 mg/kg to about 1000 mg/kg/day in single or divided doses, preferably about 1 mg/kg/day to about 200 mg/kg/day for an average subject, depending upon the 3-hydroxy-3-methylglutaryl coenzyme A reductase inhibitor and the route of administration. However, some variation in dosage will necessarily occur depending on the condition of the subject being treated. The individual responsible for dosing will, in any event, determine the appropriate dose for the individual subject.

Any thiazolidinedione antidiabetic agent may be used in the combination compositions, combination therapies and kits of the present invention. The term thiazolidinedione antidiabetic agent refers to a pharmaceutical agent that increases insulin sensitivity in tissues important for insulin action such as adipose tissue, skeletal muscle, and liver.

The following patents exemplify thiazolidinedione antidiabetic agents which can be used in the combination compositions, methods and kits of the present invention: U.S. Pat. No. 4,340,605; U.S. Pat. No. 4,342,771; U.S. Pat. No. 4,367,234; U.S. Pat. No. 4,617,312; U.S. Pat. No. 4,687,777 and U.S. Pat. No. 4,703,052. Preferred thiazolidinedione antidiabetic agents include pioglitazone, also known as Actos®, and rosiglitazone, also known as Avandia®.

Thiazolidinedione antidiabetic agents are preferably administered in amounts ranging from about 0.1 mg/day to about 100 mg/day in single or divided doses, preferably about 0.1 mg/day to about 50 mg/day for an average subject, depending upon the thiazolidinedione antidiabetic agent and the route of administration. However, some variation in dosage will necessarily occur depending on the condition of the subject being treated. The individual responsible for dosing will, in any event, determine the appropriate dose for the individual subject.

Any angiotensin converting enzyme (ACE) inhibitor may be used as the Second Agent in the combination compositions, combination therapies and kits of the present invention. The term angiotensin converting enzyme inhibitor refers to a pharmaceutical agent which inhibits angiotensin converting enzyme activity. Angiotensin converting enzyme is involved in the conversion of angiotensin I to the vasoconstrictor, angiotensin II. The activity of angiotensin converting enzyme inhibitors may readily be determined by methods known to those skilled in the art, including any of the standard assays described in the patents listed below.

Preferred angiotensin converting enzyme inhibitors include: alacepril, disclosed in U.S. Pat. No. 4,248,883; benazepril, disclosed in U.S. Pat. No. 4,410,520; captopril, disclosed in U.S. Pat. Nos. 4,046,889 and 4,105,776; ceronapril, disclosed in U.S. Pat. No. 4,452,790; delapril, disclosed in U.S. Pat. No. 4,385,051; enalapril, disclosed in U.S. Pat. No. 4,374,829; fosinopril, disclosed in U.S. Pat. No. 4,337,201; imadapril, disclosed in U.S. Pat. No. 4,508,727; lisinopril, disclosed in U.S. Pat. No. 4,555,502; moexipril, disclosed in U.S. Pat. No. 4,344,949; moveltopril, disclosed in Belgian Patent No. 893,553; perindopril, disclosed in U.S. Pat. No. 4,508,729; quinapril and its hydrochloride salt, disclosed in U.S. Pat. No. 4,344,949; ramipril, disclosed in U.S. Pat. No. 4,587,258; spirapril, disclosed in U.S. Pat. No. 4,470,972; temocapril, disclosed in U.S. Pat. No. 4,699,905; and trandolapril, disclosed in U.S. Pat. No. 4,933,361. The disclosures of all such patents are incorporated herein by reference.

Angiotensin converting enzyme inhibitors are preferably administered in amounts ranging from about 0.01 mg/kg/day to about 500 mg/kg/day in single or divided doses, preferably about 10 mg to about 300 mg per day for an average subject, depending upon the angiotensin converting enzyme inhibitor and the route of administration. However, some variation in dosage will necessarily occur depending on the condition of the subject being treated. The individual responsible for dosing will, in any event, determine the appropriate dose for the individual subject.

Any angiotensin-II receptor (A-II) antagonist may be used as the Second Agent in the combination compositions, combination therapies and kits of the present invention. The term angiotensin-II receptor antagonist refers to a pharmaceutical agent that blocks the vasoconstrictor effects of angiotensin II by blocking the binding of angiotensin II to the $AT_1$ receptor found in many tissues, (e.g., vascular smooth muscle, adrenal gland). The activity of angiotensin-II receptor antagonist may readily be determined by methods known to those skilled in the art, including any of the standard assays described in the patents listed below.

Angiotensin-II receptor antagonists include: candesartan, which may be prepared as disclosed in U.S. Pat. No. 5,196,444; eprosartan, which may be prepared as disclosed in U.S. Pat. No. 5,185,351; irbesartan, which may be prepared as disclosed in U.S. Pat. No. 5,270,317; losartan, which may be prepared as disclosed in U.S. Pat. No. 5,138,069; and valsartan, which may be prepared as disclosed in U.S. Pat. No. 5,399,578. The disclosures thereof are incorporated herein by reference. More preferred angiotensin-II receptor antagonists are losartan, irbesartan and valsartan.

Angiotensin-II receptor antagonists are preferably administered in amounts ranging from about 0.01 mg/kg/day to about 500 mg/kg/day in single or divided doses, preferably about 10 mg to about 300 mg per day for an average subject, depending upon the angiotensin-II receptor antagonist and the route of administration. However, some variation in dosage will necessarily occur depending on the condition of the subject being treated. The individual responsible for dosing will, in any event, determine the appropriate dose for the individual subject.

Any γ-aminobutyric acid (GABA) agonist may be used as the Second Agent in the combination compositions, combination therapies and kits of the present invention. The term γ-aminobutyric acid agonist refers to a pharmaceutical agent that binds to GABA receptors in the mammalian central nervous system. GABA is the major inhibitory neurotransmitter in the mammalian central nervous system. The activity of γ-aminobutyric acid (GABA) agonist may readily be determined by methods known to those skilled in the art, including the procedures disclosed in Janssens de Verebeke, P. et al., Biochem. Pharmacol., 31, 2257–2261 (1982), Loscher, W., Biochem. Pharmacol., 31, 837–842, (1982) and/or Phillips, N. et al., Biochem. Pharmacol., 31, 2257–2261.

Preferred γ-aminobutyric acid agonists, which may be prepared by procedures available in the art, include: muscimol, progabide, riluzole, baclofen, gabapentin (Neurontin®), vigabatrin, valproic acid, tiagabine (Gabitril®), lamotrigine (Lamictal®), pregabalin, pagoclone, phenytoin (Dilantin®), carbamazepine (Tegretol®), topiramate (Topamax®) and analogs, derivatives, prodrugs and pharmaceutically acceptable salts of those γ-aminobutyric acid agonist agonists.

In general, in accordance with the present invention, the γ-aminobutyric acid agonist used in the combinations, pharmaceutical compositions, methods and kits of the present invention will be administered in a dosage amount of about 4 mg/kg body weight of the subject to be treated per day to about 60 mg/kg body weight of the subject to be treated per day, in single or divided doses. However, some variation in dosage will necessarily occur depending upon the condition of the subject being treated. The person responsible for administration will, in any event, determine the appropriate dose for the individual subject. In particular, when used as the γ-aminobutyric acid agonist agonist in the present invention, pregabalin will be dosed at about 300 mg to about 1200 mg per day; gabapentin will be dosed at about 600 mg to about 3600 mg per day.

Any phosphodiesterase type 5 (PDE-5) inhibitor may be used as the Second Agent in the combination compositions, combination therapies and kits of the present invention. The term phosphodiesterase type 5 inhibitor refers to any substance or agent or any combination of substances and/or agents which reduces, retards, or eliminates the enzymatic action of cyclic guanosine monophosphate (cGMP)-specific phosphodiesterase type 5. Such actions are readily determined by those skilled in the art according to assays as described in PCT application publication WO 00/24745.

The following patent publications exemplify phosphodiesterase type 5 inhibitors which can be used in the combination compositions, methods and kits of the present invention, and refer to methods of preparing those phosphodiesterase type 5 (PDE-5) inhibitors: PCT application publication WO 00/24745; PCT application publication WO 94/28902; European Patent application publication 0463756A1; European Patent application publication 0526004A1 and European Patent application publication 0201188A2. A preferred phosphodiesterase type 5 inhibitor is sildenafil citrate, also known as VIAGRA®.

Suitable cGMP PDE5 inhibitors for the use according to the present invention include: the pyrazolo [4,3-d] pyrimidin-7-ones disclosed in EP-A-0463756; the pyrazolo [4,3-d]pyrimidin-7-ones disclosed in EP-A-0526004; the pyrazolo [4,3-d pyrimidin-7-ones disclosed in published international patent application WO 93/06104; the isomeric pyrazolo [3,4-d]pyrimidin-4-ones disclosed in published international patent application WO 93/07149; the quinazolin-4-ones disclosed in published international patent application WO 93/12095; the pyrido [3,2-d] pyrimidin-4-ones disclosed in published international patent application WO 94/05661; the purin-6-ones disclosed in published international patent application WO 94/00453; the pyrazolo [4,3-d]pyrimidin-7-ones disclosed in published international patent application WO 98/49166; the pyrazolo [4,3-d]pyrimidin-7-ones disclosed in published international patent application WO 99/54333; the pyrazolo [4,3-d] pyrimidin-4-ones disclosed in EP-A-0995751; the pyrazolo [4,3-d]pyrimidin-7-ones disclosed in published international patent application WO 00/24745; the pyrazolo [4,3-d] pyrimidin-4-ones disclosed in EP-A-0995750; the compounds disclosed in published international application WO95/19978; the compounds disclosed in published international application WO 99/24433; the compounds disclosed in published international application WO 93/07124; the compounds disclosed in international patent application PCT IB 00/01457 filed on 11$^{th}$ Oct. 2000 and the compounds disclosed in international patent application PCT IB 00/01430 filed on 4$^{th}$ Oct. 2000. It is to be understood that the contents of the above published patent applications, and in particular the general formulae and exemplified compounds therein are incorporated herein in their entirety by reference thereto.

Preferred type V phosphodiesterase inhibitors for the use according to the present invention include: 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756); 5-(2-ethoxy-5-morpholinoacetylphenyl)-1-methyl-3-n-propyl-1,6-dihydro-7H-pyrazolo[4,3-d] pyrimidin-7-one (see EP-A-0526004); 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d] pyrimidin-7-one (see WO98/49166); 3-ethyl-5-[5-(4-ethylpiperazin-1-ylsulphonyl)-2-(2-methoxyethoxy) pyridin-3-yl]-2-(pyridin-2-yl)methyl-2,6-dihydro-7H-pyrazolo[4,3-d]pyrimidin-7-one (see WO99/54333); (+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d] pyrimidin-7-one, also known as 1-{6-ethoxy-5-[3-ethyl-6, 7-dihydro-2-(2-methoxyethyl)-7-oxo-2H-pyrazolo[4,3-d] pyrimidin-5-yl]-3-pyridylsulphonyl}-4-ethylpiperazine (see PCT IB 00/01457); 5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see PCT IB 00/01457); 5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see PCT IB 00/01457); 5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see PCT IB 00/01430); 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see PCT IB 00/01430); (6R,12aR)-2,3,6,7,12,12a-hexahydro-2-methyl-6-(3,4-methylenedioxyphenyl)-pyrazino[2',1':6,1]pyrido[3,4-b] indole-1,4-dione (IC-351), i.e. the compound of examples 78 and 95 of published international application WO95/19978, as well as the compound of examples 1, 3, 7 and 8; 2-[2-ethoxy-5-(4-ethyl-piperazin-1-yl-1-sulphonyl)- phenyl]-5-methyl-7-propyl-3H-imidazo[5,1-f][1,2,4]triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; and the compound of example 11 of published international application WO93/07124 (EISAI); and compounds 3 and 14 from Rotella D P, J. Med. Chem., 2000, 43, 1257.

Still other type cGMP PDE5 inhibitors useful in conjunction with the present invention include:4-bromo-5-(pyridylmethylamino)-6-[3-(4-chlorophenyl)-propoxy]-3(2H)pyridazinone; 1-[4-[(1,3-benzodioxol-5-ylmethyl)amiono]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & 38-9456 (Bayer) and Sch-51866.

Highly preferred herein are sildenafil, IC-351, vardenafil, 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one.

The suitability of any particular cGMP PDE5 inhibitor can be readily determined by evaluation of its potency and selectivity using literature methods followed by evaluation of its toxicity, absorption, metabolism, pharmacokinetics, etc in accordance with standard pharmaceutical practice. Preferably, the cGMP PDE5 inhibitors have an IC50 at less than 100 nanomolar, more preferably, at less than 50 nanomolar, more preferably still at less than 10 nanomolar. IC50 values for the cGMP PDE5 inhibitors may be determined using established literature methodology, for example as described in EP0463756-B1 and EP0526004-A1. Preferably the cGMP PDE5 inhibitors used in the invention are selective for the PDE5 enzyme. Preferably they are selective over PDE3, more preferably over PDE3 and PDE4. Preferably, the cGMP PDE5 inhibitors of the invention have a selectivity ratio greater than 100 more preferably greater than 300, over PDE3 and more preferably over PDE3 and PDE4. Selectivity ratios may readily be determined by the skilled person. IC50 values for the PDE3 and PDE4 enzyme may be determined using established literature methodology, see S A Ballard et al, Journal of Urology, 1998, vol. 159, pages 2164–2171.

Phosphodiesterase type 5 inhibitors are preferably administered in amounts ranging from about 5 mg/day to about 500 mg/day in single or divided doses, preferably about 10 mg/day to about 250 mg/day, for an average subject depending upon the phosphodiesterase type 5 inhibitor and the route of administration. However, some variation in dosage will necessarily occur depending on the condition of the subject being treated. The individual responsible for dosing will, in any event, determine the appropriate dose for the individual subject.

Any adenosine agonist may be used as the Second Agent in the combination compositions, combination therapies and kits of the present invention. The term adenosine agonist refers to any substances and/or agents which pharmacologically affect the cardioprotective effects of ischemic preconditioning by activating adenosine A-3 receptors.

The utility of the adenosine agonists as medical agents in the treatment of cardiac tissue ischemia is demonstrated by the activity of said agonists in conventional preclinical cardioprotection assays (see the in vivo assay in Klein, H. et al., Circulation 92:912–917 (1995); the isolated heart assay in Tracey, W. R. et al., Cardiovascular Research 33:410–415 (1997); the antiarrhythmic assay in Yasutake M. et al., Am. J. Physiol., 36:H2430–H2440 (1994); the NMR assay in Kolke et al., J. Thorac. Cardiovasc. Surg. 112: 765–775 (1996)) and the additional in vitro and in vivo assays described below. Such assays also provide a means whereby the activities of adenosine agonists can be compared with the activities of other known compounds. The results of these comparisons are useful for determining dosage levels in mammals, including humans, for the treatment of such diseases.

Human Adenosine A1 and A3 Receptor Assays

Materials: Full-length human adenosine $A_1$ and $A_3$ receptor cDNA's subcloned into the eukaryotic expression vector pRcCMV (Invitrogen) were purchased from The Garvan Institute, Sydney, Australia. Chinese hamster ovary (CHO-K1) cells were obtained from the American Type Tissue Culture Collection (Rockville, Md., USA). DMEM and DMEM/F12 culture media and foetal calf serum were obtained from Gibco-BRL (Grand Island, N.Y., USA). The A1/A3 adenosine receptor agonist N6-(4-amino-3-[125I]iodobenzyl)adenosine ($^{125}$I-ABA) was prepared by New England Nuclear (Boston, Mass., USA). Adenosine deaminase (ADA) was obtained from Boehringer Mannheim (Indianapolis, Ind., USA). The phosphodiesterase inhibitor RO-20-1724 was obtained from Research Biochemicals International (Natick, Mass., USA).

Expression of Human Adenosine A1 and A3 Receptors

For stable expression studies, adenosine receptor $A_1$ and $A_3$ expression plasmids (20 µg) are transfected into CHO-K1 cells, or HEK 293s cells, respectively, grown in DMEM/F12 (CHO) or DMEM (HEK 293s), with 10% foetal calf serum media, using a calcium phosphate mammalian cell transfection kit (5 Prime-3 Prime). Stable transfectants are obtained by selection in complete media containing 500 µg/ml (CHO) or 700 µg/ml (HEK 293s) active neomycin (G418) and screened for expression by [$^{125}$I]-ABA binding.

Receptor Membrane Preparation

Cells stably expressing either human $A_1$ or human $A_3$ receptors are collected by centrifugation at 300×g for 5 minutes, the supernatant is discarded and the cell pellet is resuspended in cell buffer consisting of (mmoles/L): HEPES (10), $MgCl_2$ (5), PMSF (0.1), bacitracin (100 µg/ml), leupeptin (10 µg/ml), DNAse I (100 µg/ml), ADA (2 U/ml), pH 7.4. Crude cell membranes are prepared by repeated aspiration through a 21 gauge needle, collected by centrifugation at 60,000×g for 10 minutes and stored in cell buffer at −80° C.

Estimation of Compound Binding Affinity Constants ($K_i$)

Receptor membranes are resuspended in incubation buffer consisting of (mmoles/L): HEPES (10), EDTA (1), MgCl$_2$ (5), pH 7.4. Binding reactions (10–20 µg membrane protein) are carried out for one hour at room temperature in 250 µl incubation buffer containing 0.1 nM of $^{125}$I-ABA (2200 Ci/mmol) and increasing concentrations of compound (0.1 nM–30 µM). The reaction is stopped by rapid filtration with ice-cold PBS, through glass fibre filters (presoaked in 0.6% polyethylenimine) using a Tomtec 96-well harvester (Orange, Conn., USA). Filters are counted in a Wallac Microbeta liquid scintillation counter (Gaithersberg, Md., USA). Nonspecific binding is determined in the presence of 5 µM I-ABA. Compound inhibitory constants ($K_i$) are calculated by fitting binding data via nonlinear least squares regression analysis to the equation: % Inhibition=100/[1+ $(10^C/10^X)^D$], where X=log[compound concentration], C (IC$_{50}$)=log[compound concentration at 50% inhibtion], and D=the Hill slope. At the concentration of radioligand used in the present study (10 fold<K$_D$), IC$_{50}$=K$_i$.

Assessment of Human Adenosine A3 Receptor Agonist Activity

Adenosine A3 agonist activity is assessed by compound inhibition of isoproterenol-stimulated cAMP levels. HEK293s cells stably transfected with human A3 receptors (as described above) are washed with Phosphate Buffered Saline (PBS) (Ca/Mg-free) and detached with 1.0 mM EDTA/PBS. Cells are collected by centrifugation at 300×g for 5 minutes and the supernatant discarded. The cell pellet is dispersed and resuspended in cell buffer (DMEM/F12 containing 10 mM HEPES, 20 µM RO-20-1724 and 1 U/ml ADA). Following preincubation of cells (100,000/well) for 10 min at 37° C., 1 µM isoproterenol, with or without increasing concentrations (0.1 nM–300 nM) test compound, and the incubation is continued for 10 min. Reactions are terminated by the addition of 1.0 N HCl followed by centrifugation at 2000×g for 10 minutes. Sample supernatants (10 µl) are removed and cAMP levels determined by radioimmunoassay (New England Nuclear, Boston, Mass., USA). The basal and control isoproterenol-stimulated cAMP accumulation (pmol/ml/100,000 cells) are routinely 3 and 80, respectively. Smooth curves are fitted to the data via nonlinear least squares regression analysis to the equation: % isoproterenol-stimulated cAMP=100/[1+$(10^X/10^C)^D$], where X=log[compound concentration], C (IC$_{50}$)=log [compound concentration at 50% inhibition], and D=the Hill slope.

The results from an in vitro test, such as that described in Tracey et al., Cardiovasc. Res., 33:410–415, 1997, demonstrate that adenosine agonists induce significant cardioprotection relative to the control group. The following patent publications exemplify adenosine agonists which can be used in the combination compositions, methods and kits of the present invention, and refer to methods of preparing those adenosine agonists: U.S. Pat. No. 5,604,210; U.S. Pat. No. 5,688,774; U.S. Pat. No. 5,773,423; J. Med. Chem. 1994, 37, 636–646; J. Med. Chem. 1995, 38, 1174–1188; J. Med. Chem. 1995, 38, 1720–1735.

U.S. Pat. No. 5,817,760 discloses recombinant human adenosine receptors A1, A2a, A2b, and A3 which were prepared by cDNA cloning and polymerase chain reaction techniques. The recombinant adenosine receptors can be utilized in an assay to identify and evaluate entities that bind to or enhance binding to adenosine receptors.

Adenosine agonists are preferably administered in amounts ranging from about 0.001 mg/kg/day to about 100 mg/kg/day, for an average subject depending upon the adenosine agonist and the route of administration. An especially preferred dosage is about 0.01 mg/kg/day to about 50 mg/kg/day of an adenosine agonists. However, some variation in dosage will necessarily occur depending upon the condition of the subject being treated. The individual responsible for dosing will, in any event, determine the appropriate dose for the individual subject.

Any compound having activity as a CETP inhibitor can serve as the Second Agent in the combination compositions, combination therapies and kits of the present invention. The term CETP inhibitor refers to compounds that inhibit the cholesteryl ester transfer protein (CETP) mediated transport of various cholesteryl esters and triglycerides from HDL to LDL and VLDL. A variety of these compounds are described and referenced below, however other CETP inhibitors will be known to those skilled in the art. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8): 815–816 (1996), and *Bioorg. Med. Chem. Lett.*; 6:1951–1954 (1996), respectively. Other CETP inhibitors that can be used in combination with compounds of the present invention are disclosed in WO 00/17164, WO 00/17165, WO 99/20302, EP 796846, EP818197, EP 818448, WO 99/14204, WO 99/41237, WO 95/04755, WO 96/15141, WO 96/05227, DE 19704244, DE19741051, DE 19741399, DE 19704243, DE 19709125, DE 19627430, DE 19832159, DE 19741400, JP 11049743, and JP 09059155. Preferred CETP inhibitors that can be used in combination with the compounds of the present invention include

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid propyl ester,

[2S,4S]4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;

[2S,4S]2-cyclopropyl-4-[(3,5-dichloro-benzyl)-methoxycarbonyl-amino]-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid propyl ester; and

[2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester;

and pharmaceutically acceptable salts and prodrugs thereof and salts of the prodrugs.

In the aspects of this invention related to therapeutic methods of treating or preventing diabetic complications wherein a compound of formula I of this invention and a Second Agent are administered together as part of the same pharmaceutical composition and to methods wherein these two agents are administered separately, the appropriate dosage regimen, the amount of each dose administered and the intervals between doses of the active agents will again depend upon the compound of formula I of this invention and the Second Agent being used, the type of pharmaceutical compositions being used, the characteristics of the subject being treated and the severity of the condition, disease, symptom or complication being treated.

The compounds of the present invention may be administered alone or in combination with pharmaceutically acceptable vehicles, diluents or carriers, in either single or multiple doses. Suitable pharmaceutical carriers include inert solid diluents or fillers, sterile aqueous solutions and various organic solvents. The pharmaceutical compositions formed by combining the compounds of formula I of the present invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyinylpyrrolidone, sucrose, gelatin and acacia. Additionally, lubricating agents such as magnesium stearate, sodium lauryl sulfate or talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin or combinations thereof.

For parenteral administration, solutions of the compounds of the present invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Administration of the compounds of, formula I of the present invention can be via any method which delivers a compound of the present invention preferentially to the desired tissue (e.g., nerve, kidney, retina and/or cardiac tissues). These methods include oral, parenteral, topical, intraduodenal, rectal, inhalation routes, etc. Generally, the compounds of the present invention are administered in single (e.g., once daily) or multiple doses or via constant infusion.

Generally, a compound of formula I of the present invention is administered orally, or parenterally (e.g., intravenous, intramuscular, subcutaneous or intramedullary). Topical administration may also be indicated, for example, where the patient is suffering from a gastrointestinal disorder or whenever the medication is best applied to the surface of a tissue or organ as determined by the attending physician.

The amount and timing of compounds administered will, of course, be dependent on the subject being treated, on the severity of the affliction, on the manner of administration and on the judgment of the prescribing physician. Thus, because of patient to patient variability, the dosages given below are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases.

Thus, for example, in one mode of administration the compounds of formula I of the present invention may be administered just prior to surgery (e.g., within twenty-four hours before surgery, for example, cardiac surgery) during or subsequent to surgery (e.g., within twenty-four hours after surgery) where there is risk of myocardial ischemia. The compounds of formula I of the present invention may also be administered in a chronic daily mode.

The compounds of the present invention are generally administered in the form of a pharmaceutical composition comprising at least one of the compounds of formula I of this invention together with a pharmaceutically acceptable vehicle or diluent. Thus, the compounds of formula I of this invention can be administered individually or together in any conventional oral, parenteral, rectal or transdermal dosage form.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of an active ingredient, i.e, a compound of formula I of the present invention, are known, or will be apparent in light of this disclosure, to those skilled in this art. For examples of methods of preparing pharmaceutical compositions, see *Remington's Pharmaceutical Sciences*, Mack Publishing Company, Easton, Pa., 19th Edition (1995).

Pharmaceutical compositions according to the present invention may contain, for example, 0.0001%–95% of the compound(s) of the present invention. In any event, the composition or formulation to be administered will contain a quantity of a compound(s) according to the present invention in an amount effective to treat the disease/condition/complication of the subject being treated.

In the combination aspect of the present invention, a compound of formula I of the present invention and a Second Agent, as described above, can be co-administered simultaneously or sequentially in any order, or as a single pharmaceutical composition comprising a compound of formula I of the present invention and a Second Agent.

Since the present invention has an aspect that relates to the treatment of the disease/conditions/complications described herein with a combination of active ingredients which may be administered separately, the invention also relates to combining separate pharmaceutical compositions in kit form. The kit comprises two separate pharmaceutical compositions: a compound of formula I, a prodrug thereof or a salt of such compound or prodrug, and a Second Agent as described above. The kit comprises a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows: "First Week, Monday, Tuesday, . . . etc . . . Second Week, Monday, Tuesday, . . . " etc. Other variations of memory aids will be readily apparent. A "daily dose" can be a single tablet or capsule or several tablets or capsules to be taken on a given day. Also, a daily dose of a compound of formula I of the present invention can consist of one tablet or capsule while a daily dose of the Second Agent can consist of several tablets or capsules or vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of formula I of the present invention generally will be administered in a convenient formulation. The following formulation examples are illustrative only and are not intended to limit the scope of the present invention.

In the formulations which follow, "active ingredient" means a compound(s) of the present invention.

Formulation 1: Gelatin Capsules
Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
| --- | --- |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 74.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient | 25 mg–10,000 mg |
| Isotonic saline | 1,000 mL |

The solution of the above ingredients is intravenously administered to a patient.

The active ingredient in the above formulations may also be a combination of active compounds.

General Experimental Procedures

Melting points were determined on a Thomas-Hoover capillary melting point apparatus, and are uncorrected. $^1$H NMR spectra were obtained on a Bruker AM-250 (Bruker Co., Billerica, Mass.), a Bruker AM-300, a Varian XL-300 (Varian Co., Palo Alto, Calif.), or a Varian Unity 400 at about 23° C. at 250, 300, or 400 MHz for proton. Chemical shifts are reported in parts per million (δ) relative to residual chloroform (7.26 ppm), dimethylsulfoxide (2.49 ppm), or methanol (3.30 ppm) as an internal reference. The peak shapes and descriptors for the peak shapes are denoted as follows: s, singlet; d, doublet; t, triplet; q, quartet; m, multiplet; c, complex; br, broad; app, apparent. Low-resolution mass spectra were obtained under thermospray (TS) conditions on a Fisons (now Micromass) Trio 1000 Mass Spectrometer (Micromass Inc., Beverly, Mass.), under chemical-ionization (CI) conditions on a Hewlett Packard 5989A Particle Beam Mass Spectrometer (Hewlett Packard Co., Palo Alto, Calif.), or under atmospheric pressure chemical ionization (APCI) on a Fisons (now Micromass) Platform II Spectrometer. Optical rotations were obtained on a Perkin-Elmer 241 MC Polarimeter (Perkin-Elmer, Norwalk, Conn.) using a standard path length of 1 dcm at about 23° C. at the indicated concentration in the indicated solvent.

Liquid column chromatography was performed using forced flow (flash chromatography) of the indicated solvent on either Baker Silica Gel (40 μm, J. T. Baker, Phillipsburg, N.J.) or Silica Gel 60 (EM Sciences, Gibbstown, N.J.) in glass columns or using low nitrogen or air pressure in Flash 40™ or Flash 12™ (Biotage, Charlottesville, Va.) cartridges. Radial chromatography was performed using a Chromatron (Harrison Research, Palo Alto, Calif.). The terms "concentrated" and "evaporated" refer to removal of solvent using a rotary evaporator at water aspirator pressure or at similar pressures generated by a Büchi B-171 Vacobox (Brinkmann Instruments, Inc., Westbury, N.Y.) or a Büchi B-177 Vacobox with a bath temperature equal to or less than 50° C.

Reactions requiring the use of hydrogen gas at pressures greater than 1 atmosphere were run using a Parr hydrogen apparatus (Parr Instrument Co., Moline, Ill.). Unless otherwise specified, reagents were obtained from commercial sources. The abbreviations "d", "h", and "min" stand for "day(s)", "hour(s)", and "minute(s)", respectively.

EXAMPLE 1

4-(4-Hydroxymethyl-6-[1,3,5]triazin-2-yl)-piperazine-1-sulfonic acid dimethylamide Step 1

4-Dimethylsulfamoyl-piperazine-1-carboxylic acid dimethylamide

To a solution of N-N-dimethylsulfamoyl-piperazine (5.2 mmol, 1.0 g) in THF (10 mL) and triethylamine (0.75 mL) was added N,N-dimethylaminocarbamoyl chloride (0.5 mL) and the reaction was stirred for 2 h at room temperature. The precipitated triethylamine hydrochloride was filtered off and the filtrate was evaporated to obtain a white solid, which was crystallized from a 1:1 mixture of EtOAc and n-hexane to yield the title compound of Step 1 (88%).

Step 2

4-(Chloro-dimethylamino-methylene)-piperazine-1-sulfonic acid dimethylamide hydrochloride A mixture of the title compound of Step 1 (2 mmol, 530 mg) and phosphorus oxychloride (2 mmol, 0.2 mL) was heated to 110° C. for 0.5 h. After cooling the reaction solidified to yield the title compound of Step 2, which was immediately used in Step 4 below.

Step 3

2-Methoxy-N-cyano-acetamidine

To an ice-cold solution of 2-methoxyacetamidine hydrochloride (0.1 mol) in ethanol (100 mL) and triethyl amine (0.2 mol, 27.8 mL) was added dropwise a solution of cyanogen bromide in acetonitrile. After 1 hr the solvents and the excess triethylamine were removed by evaporation and water (100 mL) was added to the resulting residue. It was then extracted with EtOAc (2×100 mL). The EtOAc extract was collected, dried, filtered and the filtrate was evaporated to obtain a light yellow solid, the title product of Step 3 (72%, 8.2 g); mp 101–103° C.

Step 4

2-Chloro-4-(4-methoxymethyl-6-[1,3,5]triazin-2-yl)-piperazine-1-sulfonic acid dimethylamide The solid title compound of Step 2 was dissolved in acetonitrile (10 mL), to it was added all of the title compound of Step 3 and refluxed for 2 h. After evaporating the excess acetonitrile, a residue was obtained, which was purified by silica gel chromatography to yield the title compound of Step 4 (58%, 410 mg); mp, 143–144° C.

Step 5

4-(4-Methoxymethyl-6-[1,3,5]triazin-2-yl)-piperazine-1-sulfonic acid dimethylamide A mixture of the title compound of Step 4 (1.0 mmol, 350 mg), palladium-carbon (100 mg), ethanol (10 mL), and sodium acetate (2.4 mmol, 196 mg) was hydrogenated in a Parr shaker at 45 lbs./sq. inch (about 3.1 atm) for 1 h. The catalyst was filtered off and the filtrate was concentrated. The resulting white precipitate was filtered and the residue was purified by silica gel chromatography (eluent, methanol/methylene chloride, 9:1) to obtain the title compound of Step 5 (70%, 224 mg); mp, 78–81° C.; NMR 2.8 (s, 6H), 3.3 (m, 4H), 3.98 (s, 3H), 3.9 (m, 4H), 4.4 (s, 2H), 8.55 (s, 1H).

Step 6

4-(4-Hydroxymethyl-6-[1,3,5]triazin-2-yl)-piperazine-1-sulfonic acid dimethylamide To an ice-cold solution of the title compound of Step 5 (1.5 mmol, 474 mg) in methylene chloride (20 mL) was added dropwise a solution of boron tribromide (1M in methylene chloride, 3 mL). After 2 h, the reaction was quenched with water (5 mL) and sufficient 10% potassium hydroxide solution to raise the pH to 9. The methylene chloride layer was collected, dried, filtered and the filtrate was evaporated to a solid residue. This was crystallized from acetone to obtain the title compound of Step 6 and this Example (68%, 275 mg); mp, 157–159° C.

EXAMPLE 2

1-{4-[3R,5S-Dimethyl-4-(4-methyl-[1,3,5]triazin-2-yl)-piperazin-1-yl]-[1,3,5]triazin-2-yl}-(R) ethanol To an ice-cold solution of 2-methoxy-propinamidine (3.8 mmol, 523 mg) in absolute ethanol (5 mL) and triethylamine (7.6 mmol, 1.1 mL) was added cyanogen bromide (2.9 M in methylene chloride, 1.3 mL). After the addition, the reaction temperature was slowly raised to room temperature and stirred for 3 hr. Evaporation of all volatile liquids gave a solid residue, which was extracted with EtOAc. The EtOAc layer was washed with water and the EtOAc layer was collected, dried, filtered and the filtrate was evaporated to dryness to obtain 2-methoxy-N-cyanopropinamidine (85%, 410 mg).

To an ice-cold solution of 2,6-dimethyl piperazine (179 mmol, 20.4 g), methylene chloride (200 mL), and triethylamine (214 mmol, 29.9 mL) was added dropwise dimethylcarbamoyl chloride (179 mmol, 16.4 mL). After 4 hr the reaction was quenched with a saturated sodium bicarbonate solution and the methylene chloride layer was collected, dried, filtered and the filtrate was evaporated to dryness to obtain an orange oil, 2,6-dimethyl-piperazine-1-carboxylic acid dimethylamide (70%, 23.1 g).

A mixture of 2,6-dimethyl-piperazine-1-carboxylic acid dimethylamide and phosphorus oxychloride (51 mmol, 4.8 mL) was heated at 110° C. for 30 min. After cooling the reaction to room temperature, 2-methoxy-N-cyanopropinamidine (51 mmol, 6.5 g) and acetonitrile was added and then refluxed for 2 hr. The reaction mixture was evaporated to dryness and the residue was purified by silica gel chromatography (eluent, 9:1 methylene chloride-methanol) to obtain 2-chloro-4-(3,5-dimethyl-piperazin-1-yl)-6-(1-methoxy-ethyl)-[1,3,5]triazine (24%, 5.1 g).

A mixture of 2-chloro-4-(3,5-dimethyl-piperazin-1-yl)-6-(1-methoxy-ethyl)-[1,3,5]triazine (1.12 mmol, 321 mg), 2,4-dichloro-6-methyl triazine (1.12 mmol, 184 mg), sodium bicarbonate (2.24 mmol, 189 mg) and DMF (3 mL) was stirred at room temperature overnight and was diluted with EtOAc (20 mL) and water (30 mL). The EtOAc extract was collected, dried, filtered and the filtrate was evaporated to a residue, which was purified by silica gel chromatography (eluent, 99:1 methylene chloride-methanol) to obtain 2-chloro-4-[2-(4-chloro-6-methyl-[1,3,5]triazine-2-yl)-3R,5S-dimethyl-piperazin-1-yl]-6-(1-methoxy-ethyl)-[1,3,5]triazine (49%, 225 mg).

A mixture of 2-chloro-4-[2-(4-chloro-6-methyl-[1,3,5]triazine-2-yl)-3R,5S-dimethyl-piperazin-1-yl]-6-(1-methoxy-ethyl)-[1,3,5]triazine (051 mmol, 211 mg), Pd—C catalyst (10%, 84 mg), HCl (2 M in ether, 0.76 mmol, 0.38 mL), ammonium formate (5.1 mmol, 322 mg) and isopropanol (8 mL) was stirred at 90° C. for 2 h. After cooling the reaction it was diluted with methylene chloride (20 mL) and was filtered. The filtrate was evaporated to dryness and the residue was partitioned between chloroform and aq. saturated sodium bicarbonate. The chloroform layer was collected, dried, filtered and the filtrate was evaporated to a residue, which was purified by silica gel chromatography (eluent, 99:1 methylene chloride-methanol) to obtain 2-[3R,5S-dimethyl-2-(4-methyl-)-[1,3,5]triazine-4-yl)-piperazin-1-yl]-4-(1-methoxy-ethyl)-[1,3,5]triazine (97%, 170 mg). 2-[3R,5S-Dimethyl-2-(4-methyl-)-[1,3,5]triazine-4-yl)-piperazin-1-yl]-4-(1-methoxy-ethyl)-[1,3,5]triazine was deprotected according to the procedures set forth in Step 6 of Example 1 above to obtain 1-[4-[3R,5S-dimethyl-4-(4-methyl-[1,3,5]triazine-2-yl)-piperazin-1-yl]-[1,3,5]triazin-2-yl}-(R,S) ethanol, which was chromatographed (HPLC) using a chiral column to obtain the title compound of this Example. (76%; mp, 136–138° C.; [α]$_D$+14.4 (1.19 mg/ml, methanol)).

EXAMPLE 3

1-{4-[4-(4-Cyclopropyl-[1,3,5]triazin-2-yl)-3R,5S-dimethyl-piperazin-1-yl]-[1,3,5]triazin-2-yl}-ethanol To an ice-cold solution of 2-chloro-4-(3,5-dimethyl-piperazin-1-yl)-6-(1-methoxy-ethyl)-[1,3,5]triazine, prepared in Example 2 above, (2.2 mmol, 631 mg) in methylene chloride (7 mL) was added boron tribromide (1 M in methylene chloride, 11.04 mmol, 11 mL) and the reaction was stirred for 2 h. After the reaction was allowed to come to room temperature, methylene chloride (10 mL) was added to it followed by a small quantity of water (1 mL) to quench the unreacted boron tribromide. Sufficient saturated aq. sodium bicarbonate was added to raise the pH of the reaction solution to 8. The methylene chloride layer was collected, dried, filtered and the filtrate was evaporated to dryness to obtain a residue, which was purified by silica gel chromatography (eluent, 98:2 methylene chloride-methanol) to obtain 1-[4-chloro-6-(3,5-dimethyl-piperazin-1-yl)-[1,3,5]triazin-2-yl]-ethanol (65%, 392 mg); mp 126–128° C.

A mixture of this compound (0.74 mmol, 200 mg), 2,4-dichloro-6-cyclopropyl-triazine (0.74 mmol, 140 mg), sodium bicarbonate (1.47 mmol, 124 mg) and DMF (4 mL) was stirred at room temperature overnight and was diluted with EtOAc (20 mL) and water (20 mL). The EtOAc extract was collected, dried, filtered and the filtrate was evaporated to a white solid, 2-chloro-4-[2-(4-chloro-6-cyclopropyl-[1,3,5]triazine-2-yl)-3R,S5-dimethyl-piperazin-1-yl]-6-(1-methoxy-ethyl)-[1,3,5]triazine (98%, 306 mg).

A mixture of 2-chloro-4-[2-(4-chloro-6-cyclopropyl-[1,3,5]triazine-2-yl)-3R,S5-dimethyl-piperazin-1-yl]-6-(1-methoxy-ethyl)-[1,3,5]triazine (0.72 mmol, 306 mg), Pd—C catalyst (10%, 122 mg), HCl (2 M in ether, 1.08 mmol, 0.54 mL), ammonium formate (7.2 mmol, 454 mg) and isopropanol (7 mL) was stirred at 90° C. for 2 h. After cooling the reaction it was diluted with methylene chloride (20 mL) and was filtered. The filtrate was evaporated to dryness and the residue was partitioned between chloroform and aq. saturated sodium bicarbonate. The chloroform layer was collected, dried, filtered and the filtrate was evaporated to a residue, which was purified by silica gel chromatography (eluent, 99:1 methylene chloride-methanol) to obtain a solid, which was triturated with isopropyl ether to obtain the title compound of this Example (64%, 106 mg); mp 120–121° C.

EXAMPLE 4

Benzofuran-2-yl-{4-[4-1-hydroxy-ethyl)-[1,3,5]triazin-2-yl]-2R,6S-dimethyl-piperazin-1-yl}-methanone A mixture of 1-[4-chloro-6-(3,5-dimethyl-piperazin-1-yl)-[1,3,5]triazin-2-yl]-ethanol, prepared in Example 3 above (1.26 mmol, 457 mg), benzofuran-2-carboxylic acid chloride (1.26 mmol, 228 mg), triethylamine (2.52 mmol, 0.35 mL) and methylene chloride (6 mL) was stirred overnight at room temperature. After adding a further quantity of methylene chloride (10 mL) and aq. saturated sodium bicarbonate to the reaction, the methylene chloride layer was collected, dried, filtered and the filtrate was evaporated to dryness to obtain a brown oil (650 mg), which was immediately used in the next step. A mixture of this brown oil, Pd—C catalyst (10%, 1.3 g), HCl (2 M in ether, 2 mL), ammonium formate (1.6 g), and isopropanol (15 mL) was heated at 90° C. for 1 h. After cooling the reaction, it was diluted with methylene chloride (20 mL) and was filtered. The filtrate was evaporated to dryness and the residue was partitioned between chloroform and aq. saturated sodium bicarbonate. The chloroform layer was collected, dried, filtered and the filtrate was evaporated to a residue, which was purified by silica gel chromatography (eluent, 99:1 methylene chloride-methanol) to obtain a solid, which was triturated with isopropyl ether to obtain the title product of this Example (24%, 84 mg); mp, 99–101° C.

EXAMPLE 4A

Furo[2,3-c]pyridin-2-yl-{4-[4-1-hydroxy-ethyl)-[1,3,5]triazin-2-yl]-2R,6S-dimethyl-piperazin-1-yl}-methanone The title compound of this example was prepared according to procedures analogous to those described in Example 4, except furo[2,3-c]pyridin-2-carboxylic acid chloride was used in place of benzofuran-2-carboxylic acid chloride, mp, 99–101° C.

EXAMPLE 5

4-[4-(1-Hydroxy-ethyl)-[1,3,5]triazin-2-yl]-piperazine-1-sulfonic acid dimethylamide To a suspension of 2-benzyloxy-propionamide (*Helv. Chim. Acta*, 1971, 845–851) (26.6 mmol, 4.77 g) in acetonitrile (100 mL) at room temperature was added dropwise chlorosulfonyl isocyanate (26.6 mmol, 4.1 mL) in acetonitrile (20 mL). After 1 h the reaction was concentrated, then carefully quenched with water (20 mL) and allowed to stir at room temperature for 1 h. The precipitated solid was filtered, collected and air-dried to obtain (2-benzyloxy-propionyl)-urea (62%, 3.66 g); NMR 1.2 (d, 3H), 4.0 (t, 1H), 4.4 (dd, 2H), 7.3 (m, 5H), 7.7 (s, 1H), 10.0 (S, 1H). The above reaction conditions were followed to convert (2-benzyloxy-propionyl)-urea to 2-benzyloxy-N-ureidocarbonyl-propionamide, using the above compound, (2-benzyloxy-propionyl)-urea (16.5 mmol, 3.66 g), chlorosulfonyl isocyanate (28.8 mmol, 2.5 mL), and acetonitrile (80 mL). The yield of 2-benzyloxy-N-ureidocarbonyl-propionamide was 59% (2.56 g); NMR 1.4 (d, 3H), 4.2 (t, 1H), 4.6 (dd, 2H), 7.4 (m, 5H), 9.8 (s, 1H), 11.1 (s, 1H).

To an ice-cold suspension of 2-benzyloxy-N-ureidocarbonyl-propionamide (9.4 mmol, 2.5 g) in water (15 mL) was added KOH (28 mmol, 1.6 g) in water (10 mL). The reaction temperature was slowly raised to room temperature, and the reaction was allowed to stir for 1 h. Sufficient acetic acid was added to adjust the pH of the reaction to 5, and the resulting cloudy solution was extracted with chloroform (3×20 mL). The chloroform layer was collected, dried, filtered and the filtrate was concentrated to obtain a residue, which was triturated with isopropyl ether to obtain 6-(1-benzyloxy-ethyl)-1H-[1,3,5]triazine-2,4-dione (74%, 1.72 g); NMR 1.4 (d, 3H), 4.2 (t, 1H), 4.6 (dd, 2H), 7.4 (m, 5H), 11.2 (s, 1H), 12.1 (s, 1H).

A mixture of 6-(1-benzyloxy-ethyl)-1H-[1,3,5]triazine-2,4-dione (6.1 mmol, 1.5 g), phosphorus oxychloride (18.2 mmol, 1.7 mL), and diethyl aniline (1 mL) was heated at 70° C. for 1 h. Excess phosphorus oxychloride was removed and the residual oil was extracted with chloroform (2×20 mL); the extract was washed with water (3×20 mL); the chloroform layer was collected, dried, filtered and the filtrate was evaporated to obtain an oily product. This oily product was chromatographed over silica gel (eluent, 9:1 hexane-EtOAc) to obtain 2-(1-benzyloxy-ethyl)-4,6-dichloro-[1,3,5]triazine (35%, 611 mg); NMR 1.6 (d, 3H), 4.0 (t, 1H), 4.6 (dd, 2H), 7.3 (m, 5H).

A mixture of 2-(1-benzyloxy-ethyl)-4,6-dichloro-[1,3,5]triazine (0.75 mmol, 212 mg), NN-dimethylsulfamoyl piperazine (0.75 mmol, 144 mg), sodium bicarbonate (1.5 mmol, 125 mg), and DMF (3 mL) was stirred overnight at room temperature. EtOAc (15 mL) and water (20 mL) were added and the EtOAc extract was collected and washed with water (2×10 mL). The EtOAc layer was collected, dried and filtered, and the filtrate was evaporated to obtain 4-[4-(1-benzyloxy-ethyl)-6-chloro-[1,3,5]triazin-2-yl]-piperazine-1-sulfonic acid dimethylamide (97%, 320 mg); mass spectrum, m/e 441.

A mixture of 4-[4-(1-benzyloxy-ethyl)-6-chloro-[1,3,5]triazin-2-yl]-piperazine-1-sulfonic acid dimethylamide (0.73 mmol, 320 mg), (Pd—C 910%, 640 mg), HCl (2 M in ether, 4.4 mmol, 2.2 mL), ammonium formate (15 mmol, 915 mg) and isopropanol (10 mL) was heated at 90° C. for 2 h. The reaction was cooled and filtered, and to the filtrate was added chloroform (20 mL) and aq. saturated sodium bicarbonate (20 mL). The chloroform layer was collected, dried, filtered and the filtrate was evaporated to dryness. The resulting residue was purified by silica gel chromatography (eluent, 96:4 chloroform-methanol) to yield the title compound of this example (59%, 136 mg); mp 124–125° C.; NMR 1.5 (d, 3H), 2.8 (s, 6H), 3.3 (m, 4H), 4.0 (s, 4H0, 7.2 (s, 1H, 8.6 (s, 1H).

EXAMPLE 6

1-{4-[4-(4-Hydroxymethyl-[1,3,5]triazin-2-yl)-3R,5S-dimethyl-piperazin-1-yl]-[1,3,5]triazin-2-yl}-ethanol A mixture of 1-[4-chloro-6-(3,5-dimethyl-piperazin-1-yl)-[1,3,5]triazin-2-yl]-ethanol, prepared in Example 3 (0.78 mmol, 212 mg), 2,4-dichloro-6-diazomethyl-triazine (0.78 mmol, 148 mg), sodium bicarbonate (1.56 mmol, 131 mg), and DMF (3 mL) was stirred overnight at room temperature. EtOAc (15 mL) and water (20 mL) were added and the EtOAc extract was collected and washed with water (2×10 mL). The EtOAc layer was collected, dried and filtered, and the filtrate was evaporated to obtain an oily product, 2-{4-[4-(4-chloro-6-diazomethyl-[1,3,5]triazin-2-yl)-3R,5S-dimethylpiperazin-1-yl]-[1,3,5]triazin-2-yl}-ethanol (442 mg); mass spectrum m/e 425.

The crude oily product, 2-{4-[4-(4-chloro-6-diazomethyl-[1,3,5]triazin-2-yl)-3R,5S-dimethylpiperazin-1-yl]-[1,3,5]triazin-2-yl}-ethanol, was dissolved in EtOAc (10 mL) and to the solution was added 10% sulfuric acid (2 mL) and allowed to stir for 1 h. Excess EtOAc was removed and the residue was partitioned between methylene chloride (20 mL) and aq. saturated sodium bicarbonate (10 mL). The methylene chloride layer was collected, dried and filtered, and the filtrate was evaporated to obtain an oily product, 2-{4-[4-(4-chloro-6-hydroxymethyl-[1,3,5]triazin-2-yl)-3R,5S-dimethylpiperazin-1-yl]-[1,3,5]triazin-2-yl}-ethanol (43%, 184 mg), which was used in the next step without further purification, mass spectrum m/e 415.

The above product, 2-{4-[4-(4-chloro-6-hydroxymethyl-[1,3,5]triazin-2-yl)-3R,5S-dimethylpiperazin-1-yl]-[1,3,5]triazin-2-yl}-ethanol, was dechlorinated according to the procedures described in Example 3 above to obtain the title compound of this example (18%, 28 mg); mp 188–192° C.

EXAMPLE 7

2-{4-[4-(4-Hydroxymethyl-[1,3,5]triazin-2-yl)-3R,5S-dimethyl-piperazin-1-yl]-6-methyl-[1,3,5]triazin-2-yl}-phenol A mixture of 2-methoxy-benzonitrile (75.6 mmol, 10.06 g), trichloroacetonitrile (151.1 mmol, 21.8 g), and aluminum tribromide (0.76 mmol, 201 mg) was cooled to −20° C. and HCl gas was bubbled into the mixture for 20 min. After stirring the reaction mixture for 2 h at −20° C., the temperature of the reaction was allowed to come to room temperature. After overnight stirring, the reaction was quenched with water (100 mL) and extracted with EtOAc (2×200 mL). The EtOAc extract was washed with aq. saturated sodium bicarbonate (2×20 mL) and the EtOAc layer was collected, dried and filtered, and the filtrate was evaporated to a solid residue, which was purified by silica gel chromatography (eluent, 4:1 hexane-EtOAc) to obtain 1-(2-methoxyphenyl)-3,5-bis-trichloromethyl-triazine (26%, 8.4 g); mp 93–95° C.

A mixture of 1-(2-methoxyphenyl)-3,5-bis-trichloromethyl-triazine (4.74 mmol, 2 g), 2,6-dimethyl piperazine (4.74 mmol, 541 mg), sodium bicarbonate (9.48 mmol, 797 mg), and DMF (10 mL) was stirred overnight at room temperature. Water (30 mL) and EtOAc (30 mL) were added to the reaction. The EtOAc layer was collected, dried and filtered, and the filtrate was evaporated to obtain a thick liquid, which was 2-(3,5-dimethyl-piperazin-1-yl)-4-(2-methoxy-phenyl)-6-trichloromethyl-[1,3,5]triazine (95%, 1.88 g); mass spectrum m/e 416.

The above thick liquid (4.51 mmol, 1.88 g), Pd—C catalyst (10%, 752 mg), HCl (2 M in ether, 3.4 mL), ammonium formate (2.84 g), and methanol (50 mL) were refluxed for 1 h. After cooling the reaction, it was filtered. The filtrate was evaporated to dryness and the residue was partitioned between chloroform (100 mL) and aq. saturated sodium bicarbonate. The chloroform layer was collected, dried and filtered, and the filtrate was evaporated to obtain a solid, which was 2-(3,5-dimethyl-piperazin-1-yl)-4-(2-methoxy-phenyl)-6-methyl-[1,3,5]triazine (82%, 1.16 g); mass spectrum m/e 313.

To an ice-cold solution of 2-(3,5-dimethyl-piperazin-1-yl)-4-(2-methoxy-phenyl)-6-methyl-[1,3,5]triazine (3.57 mmol, 1.12 g) in methylene chloride (50 mL) was added dropwise boron tribromide (1 M in methylene chloride, 17.9 mL) and stirred for 2 h. The reaction was diluted with methylene chloride (100 mL), quenched with water (30 mL) and saturated bicarbonate solution (20 mL). The methylene chloride layer was collected, dried, filtered, and the filtrate was evaporated to obtain a brown solid, which was purified by silica gel chromatography (eluent, 98:2 chloroform-methanol) to obtain a tan solid, which was 2-[4-(3,5-dimethyl-piperazin-1-yl)-6-methyl-[1,3,5]triazin-2-yl]-phenol (37%, 391 mg); mass spectrum m/e 299.

A mixture of 2-[4-(3,5-dimethyl-piperazin-1-yl)-6-methyl-[1,3,5]triazin-2-yl]-phenol (0.84 mmol, 250 mg), 2,4-dichloro-6-diazomethyl-triazine (0.84 mmol, 159 mg), sodium bicarbonate (1.67 mmol, 317 mg), and DMF (5 mL) was stirred overnight at room temperature. EtOAc (15 mL) and water (20 mL) were added and the EtOAc extract was collected and washed with water (2×10 mL). The EtOAc layer was collected, dried and filtered, and the filtrate was evaporated to obtain a brown semi-solid (183 mg), which was 2-{4-[4-(4-chloro-6-diazomethyl-[1,3,5]triazin-2-yl)-3,5-dimethyl-piperazin-1-yl]-6-methyl-[1,3,5]triazin-2-yl}-phenol, mass spectrum m/e 452.

The brown semi-solid (183 mg) was dissolved in EtOAc (10 mL) and to the solution was added 10% sulfuric acid (2 mL) and allowed to stir for 1 hr. Excess EtOAc was removed and the residue was partitioned between methylene chloride (20 mL) and aq. saturated sodium bicarbonate (10 mL). The methylene chloride layer was collected, dried and filtered, and the filtrate evaporated to obtain an oily product (36%, 64 mg), which was 2-{4-[4-(4-chloro-6-hydroxymethyl-[1,3,5]triazin-2-yl)-3,5-dimethyl-piperazin-1-yl]-6-methyl-[1,3,5]triazin-2-yl}-phenol, and which was used in the next step without further purification; mass spectrum m/e 443.

A mixture of 2-{4-[4-(4-chloro-6-hydroxymethyl-[1,3,5]triazin-2-yl)-3,5-dimethyl-piperazin-1-yl]-6-methyl-[1,3,5]triazin-2-yl}-phenol (0.145 mmol, 64 mg), Pd—C catalyst (10%, 64 mg), HCl (2 M in ether, 0.217 mmol, 0.11 mL), ammonium formate (1.45 mmol, 91 mg) and isopropanol (5 mL) was stirred at 90° C. for 2 h. After cooling the reaction, it was diluted with methylene chloride (20 mL) and was filtered. The filtrate was evaporated to dryness and the residue was partitioned between chloroform and aq. saturated sodium bicarbonate. The chloroform layer was collected, dried and filtered, and the filtrate was evaporated to a residue, which was purified by silica gel chromatography (eluent, 99:1 methylene chloride-methanol) to obtain a solid, which was triturated with isopropyl ether to obtain the title compound of this example (54%, 32 mg); mp 188–190° C.

EXAMPLE 8

Dimethylamino-acetic acid 1-{4-[3R,5S-dimethyl-4-(4-methyl-[1,3,5]triazin-2-yl)-piperazin-1-yl]-[1,3,5]triazin-2-yl}-ethyl ester A mixture of the title compound of Example 2, 1-{4-[3,5-dimethyl-4-(4-methyl-[1,3,5]triazin-2-yl)-piperazin-1-yl]-[1,3,5]triazin-2-yl}-ethanol, (0.45 mmol, 150 mg), N,N-dimethylaminoacetyl chloride (2.7 mmol, 440 mg) and triethyl amine (5.4 mmol, 0.75 mL) was refluxed overnight. The reaction mixture was evaporated to a residue, which was purified by silica gel chromatography (eluent, 94:6 methylene chloride-methanol) to obtain the title compound of this example (which is also the prodrug of the title compound of Example 2) as a viscous oil (30%, 56 mg); NMR 1.2 (m, 6H), 1.6 (d, 3H0, 2.4 (m, 9H), 3.3 (s, 2H), 4.7 (m, 2H), 5.0 (m, 2H), 5.6 (q, 1H), 8.45 (s, 1H), 8.55(s, 1H).

EXAMPLE 9

1-(4-{4-[4-(1-Hydroxy-ethyl)-[1,3,5]triazin-2-yl]-2R,6S-dimethyl-piperazin-1-yl}-[1,3,5]triazin-2-yl)-ethanol A mixture of 2-chloro-4-(3,5-dimethyl-piperazin-1-yl)-6-(1-methoxy-ethyl)-[1,3,5]triazine, prepared as described in Example 2 above (1.45 mmol, 525 mg), 2-(1-benzyloxy-ethyl)-4,6-dichloro-[1,3,5]triazine, prepared as described in Example 5 above (1.45 mmol, 412 mg), sodium bicarbonate (291 mmol, 243 mg), and DMF (8 mL) was stirred overnight at room temperature. EtOAC (30 mL) and water (30 mL) were added to the reaction mixture. The EtOAc layer was collected, dried, filtered and evaporated to dryness to obtain a yellow oil, 1-{4-(4-[4-(1-benzyloxy-ethyl)-[1,3,5]triazin-2-yl]-2R,6S-dimethyl-piperazin-1-yl-3-(1-methoxy-ethyl)}-[1,3,5]triazine (92%, 812 mg); mass spectrum m/e 609.

A mixture of this oil, 1-{4-(4-[4-(1-benzyloxy-ethyl)-[1,3,5]triazin-2-yl]-2R,6S-dimethyl-piperazin-1-yl-3-(1-methoxy-ethyl)}-[1,3,5]triazine (0.279 mmol, 170 mg), Pd—C catalyst (10%, 200 mg), HCl (2 M in ether, 0.837 mmol, 0.42 mL), ammonium formate (5.58 mmol, 352 mg) and isopropanol (6 mL) was stirred at 90° C. for 2 h. After cooling the reaction, it was diluted with methylene chloride (20 mL) and was filtered. The filtrate was evaporated to dryness and the residue was partitioned between chloroform and aq. saturated sodium bicarbonate. The chloroform layer was collected, dried and filtered, and the filtrate was evaporated to a residue, which was purified by silica gel chromatography (eluent, 96:4 methylene chloride-methanol) to obtain a solid, which was triturated with isopropyl ether to obtain the title compound of this Example (44%, 44 mg); mp 142–144° C.

EXAMPLES 10–15

Following procedures analogous to those described above, particularly in Examples 2, 3, 6 and 9, the following compounds of the present invention were prepared:

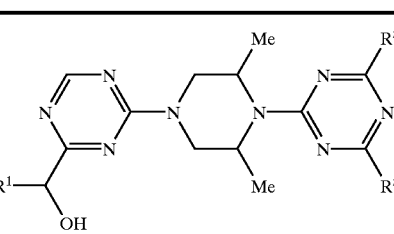

| Example No. | $R^1$ | $R^{z1}$ | $R^{z2}$ | Physico-chemical Data |
|---|---|---|---|---|
| 10 | H | H | Ph | mp 206–207° C. |
| 11 | H | H | CH$_2$OH | mp 224–225° C. |
| 12 | H | CH$_3$ | OCH$_3$ | mp 155–160° C. |
| 13 | CH$_3$ | H | Ph | NMR 1.14(s, 3H), 1.22(s, 3H), 1.28(d, 3H), 3.24(m, 2H), 3.9(s, 1H), 4.65 9q, 1H), 4.8(m, 2H), 5.1(s, 2H), 7.5(m, 3H), 8.4(m, 2H0, 8.55(s, 1H), 8.68(s, 1H) |

-continued

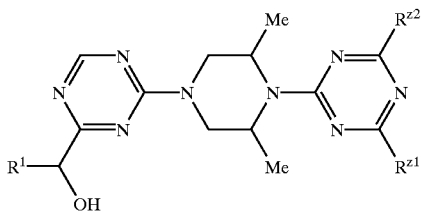

| Example No. | $R^1$ | $R^{z1}$ | $R^{z2}$ | Physico-chemical Data |
|---|---|---|---|---|
| 14 | $CH_3$ | OH | Ph | mp >275° C. |
| 15 | $CH_3$ | OH | $CH_3$ | mp 263–265° C. |

The above compounds in Examples 10-15 may be named as follows:
Example 10
1-{4-[4-(4-phenyl-[1,3,5]triazin-2-yl)-3R,5S-dimethyl-piperazin-1-yl]-[1,3,5]triazin-2-yl}-methanol;
Example 11
1-{4-[4-(4-Hydroxymethyl-[1,3,5]triazin-2-yl)-3R,5S-dimethyl-piperazin-1-yl]-[1,3,5]triazin-2-yl}-methanol;
Example 12
1-{4-[4-(4-methoxy-6-methyl-[1,3,5]triazin-2-yl)-3R,5S-dimethyl-piperazin-1-yl]-[1,3,5]triazin-2-yl}-methanol;
Example 13
1-{4-[4-(4-phenyl-[1,3,5]triazin-2-yl)-3R,5S-dimethyl-piperazin-1-yl]-[1,3,5]triazin-2-yl}-ethanol;
Example 14
1-{4-[4-(4-Hydroxy-6-phenyl-[1,3,5]triazin-2-yl)-3R,5S-dimethyl-piperazin-1-yl]-[1,3,5]triazin-2-yl}-ethanol;
Example 15
1-{4-[4-(4-Hydroxy-3-methyl-[1,3,5]triazin-2-yl)-3R,5S-dimethyl-piperazin-1-yl]-[1,3,5]triazin-2-yl}-ethanol.

EXAMPLES 16 AND 17

Following procedures analogous to those described above, particularly in Example 7, the following compounds of the invention were prepared:

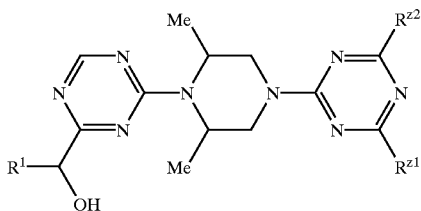

| Example No. | $R^1$ | $R^{z1}$ | $R^{z2}$ | Physico-chemical Data |
|---|---|---|---|---|
| 16 | H | H | Ph | mp, 197–198° C. |
| 17 | H | H | $CH_2OMe$ | mp, 145–150° C. |

The above compounds in Examples 16 and 17 may be named as follows:
Example 16
1-{4-[4-(4-Phenyl-[1,3,5]triazin-2-yl)-2R,6S-dimethyl-piperazin-1-yl]-[1,3,5]triazin-2-yl}-methanol;
Example 17
1-{4-[4-(4-methoxymethyl-[1,3,5]triazin-2-yl)-2R,6S-dimethyl-piperazin-1-yl]-[1,3,5]triazin-2-yl}-methanol.

What is claimed is:

1. A compound of formula I

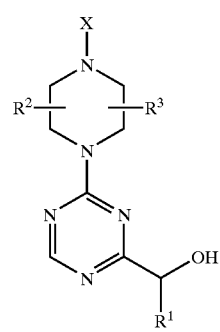

I a stereoisomer thereof, a prodrug of said compound or stereoisomer, or a pharmaceutically acceptable salt of said compound, stereoisomer or prodrug;
wherein $R^1$ is a) hydrogen or b) —$C_1$–$C_4$)alkyl;
$R^2$ and $R^3$ are each independently a) hydrogen, b) —($C_1$–$C_4$)alkyl, c) —($C_3$–$C_6$)cyoloalkyl or d) phenyl which for each occurrence is optionally substituted with one or two substituants, each substituent is independently selected from Group Q;
X is a) —C(O)—$R^4$-Z, b) —$SO_2$—$R^4$-Z, c) —C(O)—$NR^5R^6$, d) —$SO_2$—$NR^5R^6$ or e) 1,3,5-triazin-2-yl having $R^{z1}$ and $R^{z2}$ substituents;
$R^4$ is a) a covalent bond or b) —($C_1$–$C_4$)alkyl-;
Z is a) phenyl or benzyl wherein the phenyl ring in each of these groups is optionally substituted with one or two substitutents, each substituent is independently selected from Group Q, or b) Het;
$R^5$ and $R^6$ are each independently a) hydrogen, b) —($C_1$–$C_4$)alkyl or c) ($C_3$–$C_8$)cycloalkyl; or $R^5$ and $R^6$ are taken together along with the nitrogen atom to which they are attached to form pyrrolidinyl or piperidinyl;
Het is a) pyridyl, b) thiazolyl, c) oxazolyl, d) quinolyl, e) isoqulnolyl, f) phthalizinyl, g) quinoxalyl, h) benzthlazolyl, i) benzoxazolyl, j) benzofuranyl, k) benzothinyl, l), furanopyridyl or m) thienopyridyl; wherein each of these groups is optionally substituted with one or two substituents, each substituent is independently selected from Group Q;
Group Q is a) fluoro, b) chloro, c) bromo, d) —($C_1$–$C_4$)alkyl, e) —($C_3$–$G_6$)cycloalkyl, f) —O—($C_1$–$C_4$)alkyl, g) —S—($C_1$–$C_4$)alkyl, h) —$SO_2$—($C_1$–$C_4$)alkyl, i) hydroxy or j) —($C_1$–$C_4$)alkyl-hydroxy;
$R^{z1}$ and $R^{z2}$ are each independently selected from a) hydrogen, b) hydroxy, c) chloro, d) —($C_1$–$C_4$)alkyl, e) —($C_3$–$C_6$)cycloalkyl, f) —O—($C_1$–$C_4$)alkyl, g) —($C_1$–$C_4$)alkyl-O—($C_1$–$C_4$)alkyl, h) —CHO, i) —C(O)—($C_1$–$C_4$)alkyl, j) —($C_1$–$C_6$)alkyl-hydroxy, k) phenyl which for each occurrence is optionally substituted with one or two substitutents, each substituent is independently selected from Group Q, l) pyrroyl, m) imidazolyl or n) triazolyl.

2. A compound of claim 1 wherein $R^1$ is hydrogen or methyl.

3. A compound of claim 2 wherein $R^2$ and $R^3$ are each independently a) hydrogen, b) —($C_1$–$C_4$)alkyl, c) —($C_3$–$C_6$)cycloalkyl; or d) phenyl optionally substituted with one or two substituents, each substituent is independently selected from 1) —(C$_1$–C$_4$)alkyl, 2) —(C$_3$–C$_6$) cycloalkyl, 3) —O—(C$_1$–C$_4$)alkyl, 4) fluoro or 5) chloro.

4. A compound of claim 3 wherein R$^2$ and R$^3$ are each independently hydrogen or methyl.

5. A compound of claim 4 wherein R$^2$ is hydrogen and R$^3$ is hydrogen.

6. A compound of claim 4 wherein R$^2$ is methyl and R$^3$ is methyl.

7. A compound of claim 4 wherein X is 1,3,5-triazin-2-yl having R$^{z1}$ and R$^{z2}$ substituents.

8. A compound of claim 7 wherein one of the R$^{z1}$ and R$^{z2}$ substituents is hydrogen and the other is methyl, cyclopropyl, —CH$_2$OH, —CH(CH$_3$)OH or phenyl.

9. A compound of claim 7 wherein one of the R$^{z1}$ and R$^{z2}$ substituents is methyl and the other is methoxy or phenyl optionally substituted with 2-hydroxy.

10. A compound of claim 7 wherein one of the R$^{z1}$ and R$^{z2}$ substituents is hydroxy and the other is methyl or phenyl.

11. A compound of claim 4 wherein X is —SO$_2$N(CH$_3$)$_2$.

12. A compound of claim 4 wherein X is —C(=O)-benzofuranyl.

13. A compound of claim 4 wherein X is —C(=O)-furanopyridyl.

14. A compound selected from:

4-(4-hydroxymethyl-[1,3,5]triazin-2-yl)-piperazine-1-sulfonic acid dimethylamide;

1-{4-[3R,5S-dimethyl-4-(4-methyl-[1,3,5]triazin-2-yl)-piperazine-1-yl]-1,3,5]triazin-2-yl}-R-ethanol;

1-{4-[4-(4-cyclopropyl-[1,3,5]triazin-2-yl)-3R,5S-dimethyl-piperazin-1-yl]-[1,3,5]triazin-2-yl}-ethanol;

benzofuran-2-yl-{4-[4-1-hydroxy-ethyl)-[1,3,5]triazin-2-yl]-2R,6S-dimethyl-piperazin-1-yl}-methanone;

4-[4-(1-hydroxy-ethyl)-[1,3,5]triazin-2-yl]-piperazine-1-sulfonic acid dimethylamide;

1-{4-[4-(4-hydroxymethyl-[1,3,5]triazin-2-yl)-3R,5S-dimethyl-piperazin-1-yl]-[1,3,5]triazin-2-yl}-ethanol;

2-{4-[4-(4-hydroxymethyl-[1,3,5]triazin-2-yl)-3R,5S-dimethyl-piperazin-1-yl]-6-methyl-[1,3,5]triazin-2-yl}-phenol;

dimethylamino-acetic acid 1-{4-[3R,5S-dimethyl-4-(4-methyl-[1,3,5]triazin-2-yl)-piperazin-1-yl]-[1,3,5]triazin-2-yl}-ethyl ester;

1-(4-{4-[4-(1-hydroxy-ethyl)-[1,3,5,]triazin-2-yl]-2R,6S-dimethyl-piperazin-1-yl}-[1,3,5]triazin-2-yl)-ethanol;

1-{4-[4-(4-phenyl-[1,3,5]triazin-2-yl)-2R,6S-dimethyl-piperazin-1-yl]-[1,3,5]triazin-2-yl}-methanol;

1-{4-[4-(4-hydroxy-3-methyl-[1,3,5]triazin-2-yl)-3R,5S-dimethyl-piperazin-1-yl]-[1,3,5]triazin-2-yl}-ethanol;

1-{4-[4-(4-phenyl-[1,3,5]triazin-2-yl)-3R,5S-dimethyl-piperazin-1-yl]-[1,3,5]triazin-2-yl}-methanol;

1-{4-[4-(4-methoxymethy-[1,3,5]triazin-2-yl)-2R,6S-dimethyl-piperazin-1-yl]-[1,3,5]triazin-2-yl}-methanol;

1-{4-[4-(4-hydroxymethyl-[1,3,5]triazin-2-yl)-3R,5S-dimethyl-piperazin-1-yl]-[1,3,5]triazin-2-yl}-methanol;

1-{4-[4-(4-methoxy-6-methyl-[1,3,5]triazin-2yl)-3R,5S-dimethyl-piperazin-1-yl]-[1,3,5]triazin-2-yl}-methanol;

1-{4-[4-(4-phenyl-[1,3,5]triazin-2-yl)-3R,5S-dimethyl-piperazin-1-yl]-[1,3,5]triazin-2-yl}-ethanol;

1-{4-[4-(4-hydroxy-6-phenyl-[1,3,5]triazin-2-yl)-3R,5S-dimethyl-piperazin-1-yl]-[1,3,5]triazin-2-yl}-ethanol; and furo[2,3c]pyridin-2-yl-{4-[4-1-hydroxy-ethyl)-[1,3,5]triazin-2-yl]-2R,6S-dimethyl-piperazin-1-yl}-methanone.

15. A pharmaceutical composition comprising a compound of claim 1, a prodrug thereof or a pharmaceutically acceptable salt of said compound or said prodrug and a pharmaceutically acceptable vehicle, carrier or diluent.

16. A method of inhibiting sorbitol dehydrogenase in a mammal in need of such inhibition comprising administering to said mammal a sorbitol dehydrogenase inhibiting amount of a compound of claim 1, a prodrug thereof or a pharmaceutically acceptable salt of said compound or said prodrug.

17. A method of treating diabetes in a mammal suffering from diabetes comprising administering to said mammal an effective amount of a compound of claim 1, a prodrug thereof or a pharmaceutically acceptable salt of said compound or said prodrug.

18. A method of reducing tissue damage resulting from ischemia comprising administering to a mammal in need of said treatment an effective amount of a compound of formula I of claim 1, a prodrug thereof or a pharmaceutically acceptable salt of said compound or said prodrug; wherein said ischemia is a result of an etiology independent of diabetic microangiopathy or diabetic macroanglopathy.

19. A method of claim 18 wherein the tissue is heart, brain, liver, kidney, lung, gut, skeletal muscle, spleen, pancreas, retina or intestinal tissue.

20. A method of providing a cardioprotective effect in a mammal which comprises administering to the mammal en effective amount of a compound of formula I of claim 1, a prodrug thereof or a pharmaceutically acceptable salt of said compound or said prodrug.

* * * * *